US010036728B2

United States Patent
Li et al.

(10) Patent No.: US 10,036,728 B2
(45) Date of Patent: Jul. 31, 2018

(54) ULTRASENSITIVE ION DETECTOR USING CARBON NANOTUBES OR GRAPHENE

(71) Applicant: Northeastern University, Boston, MA (US)

(72) Inventors: Bo Li, Malden, MA (US); Ji Hao, Boston, MA (US); Hyun Young Jung, Malden, MA (US); Yung Joon Jung, Lexington, MA (US); Swastik Kar, Belmont, MA (US)

(73) Assignee: Northeastern University, Boston, MA (US)

( * ) Notice: Subject to any disclaimer, the term of this patent is extended or adjusted under 35 U.S.C. 154(b) by 262 days.

(21) Appl. No.: 14/441,218

(22) PCT Filed: Nov. 12, 2013

(86) PCT No.: PCT/US2013/069654
§ 371 (c)(1),
(2) Date: May 7, 2015

(87) PCT Pub. No.: WO2014/075064
PCT Pub. Date: May 15, 2014

(65) Prior Publication Data
US 2015/0276677 A1     Oct. 1, 2015

Related U.S. Application Data

(60) Provisional application No. 61/724,589, filed on Nov. 9, 2012.

(51) Int. Cl.
*G01N 27/70*     (2006.01)
*G01N 27/62*     (2006.01)
(Continued)

(52) U.S. Cl.
CPC .............. *G01N 27/70* (2013.01); *G01N 27/62* (2013.01); *H01J 41/02* (2013.01); *H01J 47/02* (2013.01); *H01J 49/025* (2013.01)

(58) Field of Classification Search
None
See application file for complete search history.

(56) References Cited

U.S. PATENT DOCUMENTS 8,466,413 B2    6/2013   Kotani
2005/0109947 A1    5/2005   Turner
(Continued)

FOREIGN PATENT DOCUMENTS

KR      20120121511 A   *   11/2012   ............. G01N 27/70

OTHER PUBLICATIONS

Kyo et al, KR 20120121511, "Metal-oxide semiconductor gas sensor with nanostructure and manufacturing method thereof" (English Machine Translation); Published Nov. 2012.*
(Continued)

*Primary Examiner* — Vincent Q Nguyen
(74) *Attorney, Agent, or Firm* — Posternak Blankstein & Lund LLP

(57) ABSTRACT

An ion detection device has a strip of carbon-based nanomaterial (CNM) film and a chamber enclosing the CNM film. A low bias voltage is applied at the ends of the CNM film strip, and ions present in the chamber are detected by a change in the magnitude of current flowing through the CNM film under the bias. Also provided are methods for fabricating the device, methods for measuring pressure of a gas, and methods for monitoring or quantifying an ionizing radiation using the device.

19 Claims, 18 Drawing Sheets

(51) Int. Cl.
*H01J 41/02* (2006.01)
*H01J 47/02* (2006.01)
*H01J 49/02* (2006.01)

(56) References Cited

U.S. PATENT DOCUMENTS

| | | | |
|---|---|---|---|
| 2005/0184294 A1* | 8/2005 | Zhang | B82Y 10/00 |
| | | | 438/105 |
| 2008/0277577 A1* | 11/2008 | Funsten | H01J 49/0068 |
| | | | 250/287 |
| 2008/0314149 A1 | 12/2008 | Rueger | |
| 2010/0140723 A1 | 6/2010 | Kurtz | |
| 2010/0183844 A1 | 7/2010 | Xiong | |
| 2010/0308848 A1* | 12/2010 | Kaul | G01N 27/127 |
| | | | 324/693 |
| 2012/0049054 A1 | 3/2012 | Zhou | |
| 2013/0240746 A1 | 9/2013 | Murai | |
| 2013/0256525 A1 | 10/2013 | Hill, Jr. | |
| 2013/0264474 A1* | 10/2013 | Kholomeev | H01J 43/00 |
| | | | 250/287 |
| 2013/0276512 A1 | 10/2013 | Bae | |

OTHER PUBLICATIONS

An et al. Stable Aqueous Dispersions of Noncovalently Functionalized Graphene from Graphite and their Multifunctional High-Performance Applications. Nano Lett., 2010, 10 (10), pp. 4295-4301.

An et al. Optical and Sensing Properties of 1-Pyrenecarboxylic Acid-Functionalized Graphene Films Laminated on Polydimethylsiloxane Membranes. ACS Nano, 2011, 5 (2), pp. 1003-1011.

Kim et al. Voltage-switchable photocurrents in single-walled carbon nanotube-silicon junctions for analog and digital optoelectronics. NATURE Photonics, 8, pp. 239-243, 2014.

Li et al. Highly Organized Two- and Three-Dimensional Single-Walled Carbon Nanotubes-Polymer Hybrid Architectures. ACS Nano, 5 (6), pp. 4826-4834, 2011.

Kim et al. Highly Aligned Scalable Platinum-decorated Single-wall Carbon Nanotube Arrays for Nanoscale Electrical Interconnects. ACS Nano, 3 (9), pp. 2818-2826, 2009.

Helbling et al. Ultrasmall single walled carbon nanotube pressure sensors, Micro Electro Mechanical Systems, MEMS 2009. IEEE 22nd International Conference (2009).

Kim et al. Highly aligned scalable platinum-decorated single-wall carbon nanotube arrays for nanoscale electrical interconnects, ACS Nano, 3(9), 2009, 2818-2826.

Ma et al. A carbon nanotube-based radiation sensor, International Journal of Robotics and Automation, vol. 22:49-58 (2007).

Mattmann et al. Pulsed gate sweep strategies for hysteresis reduction in carbon nanotube transistors for low concentration NO2 gas detection Nanotechnology 21 : 185501 (2010).

Modi et al. Miniaturized gas ionization sensors using carbon nanotubes Nature, 424: 171-174 (2003).

Stampfer et al. Fabrication of discrete nanoscaled force sensors based on single-walled carbon nanotubes, IEEE Sens. J. , vol. 6, pp. 613-617 (2006).

Sumanesekera et al. Effects of gas adsorption and collisions on electrical transport in single-walled carbon nanotubes, Physical Review Letters, vol. 85, pp. 1096-1099 (2000).

Wang et al. A review of carbon nanotube-based gas sensors, Journal of Sensors, vol. 2009, Article ID 493904, 1-24 (2009).

Kang et al. The use of semiconducting single-walled carbon nanotube films to measure X-ray dose. Carbon, Elsevier, Oxford, GB, vol. 50, No. 6, Jan. 10, 2012 (Jan. 10, 2012), pp. 2197-2201.

Zhang et al. Single Carbon Nanotube Based Ion Sensor for Gas Detection, Nanotechnology, 2006. IEEE-NANO 2006. Sixth IEEE Conference on Cincinnati, OH, USA Jun. 17-20, 2006, Piscataway, NJ, USA, IEEE, vol. 2, Jun. 17, 2006 (Jun. 17, 2006), pp. 790-793.

Ma et al. Effect of Percolation on Electrical Conductivity in a Carbon Nanotube-Based Film Radiation Sensor, Nanotechnology, 2008. NANO '08. 8th IEEE Conference on, IEEE, Piscataway, NJ, USA, Aug. 18, 2008 (Aug. 18, 2008), pp. 259-262.

Ispirian et al. Use of single carbon nanotubes and graphene in particle detectors and beam monitors. Nuovo Cimento C Societa Italiana Di Fisica Italy, vol. 34C, No. 4, Jul. 2011 (Jul. 1, 2011), pp. 521-528.

Arbabi et al. Ionization collecting of gamma radiation using two carbon nanotube electrodes. Optoelectronics and Advanced Materials—Rapid Communications vol. 4, No. 11, Nov. 2010, p. 1891-1893.

Wang et al. A Single-Walled Carbon Nanotube Network Gas Sensing Device. Sensors 2011, 11, 7763-7772.

Wang et al. Flexible gas sensors with assembled carbon nanotube thin films for DMMP vapor detection. Sensors and Actuators B 150 (2010) 708-714.

Jesus et al. Latest Advances in Modified/Functionalized Carbon Nanotube-Based Gas Sensors. Nanomater. Nanotechnol. 2013.

Stampfer et al. Fabrication of Single-Walled Carbon-Nanotube-Based Pressure Sensors. Nano Letters. 2006 vol. 6, No. 2, pp. 233-237.

\* cited by examiner

ULTRASENSITIVE ION DETECTOR USING CARBON NANOTUBES OR GRAPHENE

CROSS-REFERENCE TO RELATED APPLICATIONS

This application claims the priority of U.S. Provisional Application No. 61/724,589 filed Nov. 9, 2012 and entitled "ULTRASENSITIVE ION DETECTOR USING CARBON NANOTUBE AND GRAPHENE, which is hereby incorporated herein by reference in its entirety.

BACKGROUND

Miniaturized devices having ultrasensitive ion detection capability are useful as ion detectors in diverse applications, including detection of radioactive material or other sources of radiation, electron/ion beam calibration, monitoring of pressure or vacuum, and detection of energetic particles from outer space. Carbon nanotubes (CNT) have been proposed as an ion sensing element in such devices (Modi et al., 2003).

Carbon nanotubes have attracted significant attention for use as sensors of gas molecules because of their extremely high surface-to-volume ratio and their hollow structure, which is advantageous for adsorption of gas molecules (Mattmann et al., 2010; and reviewed in Wang and Yeow, 2009). Generally, upon exposure of CNT to gas molecules, charge transfer occurs between the gas molecules and the CNT. As a result, the gas molecules act either as electron donors or electron acceptors, thereby changing an electrical property of the CNT (Wang and Yeow, 2009). In the case of inert gases, charge transfer between the gas molecules and the CNT is negligible; rather, it is the resistance of the degassed CNT that changes with the adsorption of inert gases (Sumanasekera et al., 2000). The change in resistance is believed to be due to the change in the electron and hole free carrier lifetimes of the CNT (Sumanasekera et al., 2000).

CNT also have been used as a sensing element in a radiation sensor, where the CNT were used to form parallel plate electrodes (Ma et al., 2007). However, for any given bias voltage, the CNT-based sensor collected a smaller amount of charge than stainless steel electrodes. Contrary to the investigators' expectation, the bias voltage could not be lowered by substituting CNT electrodes for stainless steel electrodes.

CNT in the form of single-walled carbon nanotubes (SWCNT) have been used in a micromechanical system (MEMS) as a sensor of pressure (Stampfer et al., 2006; Helbling et al., 2009). The MEMS-based sensor was made of a double layer pressure sensor membrane containing layers of $SiO_2$ and $Al_2O_3$, with the SWCNT embedded between the two layers. The SWCNT were in contact with source and drain metal electrodes, and additionally a gate electrode was used to bias the SWCNT in a transistor configuration. An applied differential pressure produced a strain in the pressure sensor membrane, which was transferred to the embedded SWCNT and resulted in a change in the resistance of the SWCNT (Yang and Han, 2000).

Despite the use of CNT in the areas of gas and pressure sensing, direct sensing of ions with high sensitivity using carbon nanomaterials and operating at low bias voltages has not been accomplished up to now.

SUMMARY OF THE INVENTION

Provided herein are carbon-based nanomaterial (CNM) film-containing devices for detecting ions, low pressure or vacuum levels, or levels of ionizing radiation; methods for fabricating the devices; and methods for measuring low pressure and detecting ionizing radiation using the devices.

An aspect of the invention is a device for detecting ions. The device includes an insulating substrate; first and second metallic contact pads disposed on a surface of the substrate; a strip of carbon-based nanomaterial (CNM) film, the strip having a first end and a second end, the first end in contact with the first pad and the second end in contact with the second pad; and a housing enclosing the substrate, pads, and CNM film and forming a chamber. A potential difference (voltage) applied across the pads causes current to flow through the CNM film, and ions present in the chamber are detected by a change in the magnitude of the current. For example, the CNM can contain or consist of single-walled carbon nanotubes (SWCNT), double-walled carbon nanotubes (DWCNT), multi-walled carbon nanotubes (MWCNT), or graphene. The SWCNT can be metallic, semiconducting, or a mixture thereof. The graphene can be a single atomic layer in thickness or it can contain two or more atomic layers of graphene sheet structure.

In certain embodiments, the device further includes an aperture in the housing for admitting ions into the chamber. In other related embodiments, the device further includes a source of the ions. The source can be inside the chamber or outside the chamber.

According to certain embodiments, the device is configured as a pressure sensor, such that the current change caused by the ions is modulated by pressure of a gas in which the device is immersed. In certain embodiments, the device is capable of measuring pressure down to at least $10^{-6}$ Torr.

In certain embodiments, the device is configured as an ionizing radiation detector, such that the housing is sealed and includes a gas that becomes ionized by radiation incident on the device.

In certain embodiments, the device further includes a display.

In certain embodiments the device further includes an amperometry circuit that measures the current through the CNM film.

In use, an electrical potential is applied across the first and second contact pads of the device. For example, the voltage applied across the pads can be in the range from about 0.01V to about 6.0V. Alternatively, the voltage can be in the range from about 0.5V to about 3.0V.

In certain embodiments the device has a gain of about $10^4$ to $10^7$.

In certain embodiments the CNM film of the device consists of a single SWCNT. In other embodiments the strip of CNM film contains multiple SWCNT and has a width in the range from about 20 nm to about 100 μm. In other embodiments, the width can be as large as desired for a given application, such as up to 1 mm, or up to 3 mm, or greater than 3 mm According to certain embodiments, the strip of CNM film has a length in the range from about 10 nm to about 100 μm, or to about 1 mm, or more than 1 mm, or more than 1 cm.

In certain embodiments, the insulating substrate includes or consists of a material selected from the group consisting of: Si, $SiO_2$, polydimethylsiloxane (PDMS), SU-8 photoresist, poly(methyl methacrylate) (PMMA), or a photoresist such as AZ® nLOF™ 2000 series photoresist or MICROPOSIT S1800 series photoresist.

In certain embodiments of the device, the thickness of the CNM film is in the range from about 11 nm to about 100 nm, and its surface area is in the range from about 200 nm$^2$ to about 1.5 mm$^2$.

Further, in certain embodiments, the weight of the device is in the range from about 100 μg to about 1 g, less than 1 mg, less than 1 g, less than 10 g, or greater than 1 g.

Another aspect of the invention is a method of measuring the pressure of a gas in an enclosed space (or measuring a vacuum in space). The method includes the steps of: providing a device as described above, configured as a pressure sensor, within said space; injecting ions into the space using the ion source of the device; measuring the current flowing through the CNM film of the device; and comparing the current to a standard curve or data set correlating current to pressure to determine the pressure of the gas in the space. In certain embodiments of the method, the pressure measured is in the range of about $10^{-3}$ Torr to about $10^{-6}$ Torr, or about $1.5 \times 10^{-5}$ to about $1.6 \times 10^{-6}$ Torr. An upper limit of measurable vacuum may be determined by the ability of the ion source to operate rather than any inherent limitation of the sensor device to detect ions. Certain ion sources, for example, require a pressure of $10^{-3}$ Torr or less for operation; however, the ion sensor could operate at above such a pressure if a suitable ion source is available.

A further aspect of the invention is a method of fabricating a device for detecting ions. The method includes the steps of: providing a substrate having an insulating surface; treating the insulating surface with plasma; submerging the plasma-treated substrate into a suspension of carbon-based nanomaterial (CNM), and removing the substrate from the suspension to produce a substrate coated with the CNM; coating the CNM-coated substrate with a layer of photoresist; patterning the photoresist using a lithography method to expose regions of CNM; etching the exposed regions of CNM; removing the photoresist to yield one or more CNM strips; optionally transferring the CNM strips to a receiving substrate using a wet contact printing process, and depositing metallic contact pads onto the ends of the CNM-coated strips. In certain embodiments of the method, the substrate includes or consists of a material selected from the group consisting of: silicon, silicon dioxide, silicon nitride, SU-8, or a photoresist such as AZ® nLOF™ 2000 series photoresist or MICROPOSIT S1800 series photoresist, and combinations thereof. In certain embodiments, treating the insulating layer with plasma is performed using inductively coupled plasma and a mixed gas flow. The mixed gas includes or consists of a mixture of $O_2$, $SF_6$, and Ar.

Another aspect of the invention is another method of fabricating a device for detecting ions. The method includes the steps of: providing a substrate having an insulating surface; treating the insulating surface with plasma; coating the insulating surface with photoresist; patterning the photoresist using a lithography method to form one or more microscale (i.e., having a dimension from about 1 μm to about 999 μm) or nanoscale (i.e., having a dimension from about 1 nm to about 999 nm) trenches in the photoresist; submerging the substrate into a suspension of carbon-based nanomaterial (CNM), and removing the substrate from the suspension whereby the trenches are filled with CNM from the suspension; removing the photoresist to leave one or more strips of CNM film on the substrate; and depositing metallic contact pads onto the ends of the CNM film strips.

In another aspect the invention includes use of any of the devices described above for detecting ions or for measuring the presence of ionizing radiation, where the ions present in the chamber are produced by the ionizing radiation upon penetrating the chamber.

Another aspect of the invention is a method for using any of the devices described above, configured as a pressure sensor, for quantifying pressure or vacuum in a space in which the device is enclosed. The method includes the steps of: measuring current flowing through the CNM film, or a change in such current flow, as a source of ions in the space is turned on to let in a known amount of ions; and comparing the current or change in current to a standard curve or data set correlating current to pressure for the amount of ions added by the source.

Another aspect of the invention is a method of monitoring ionizing radiation in an environment. The method includes the steps of: exposing any of the above described devices, which is configured as an ionizing radiation detector, to the environment; and measuring current flow, or a change in current flow, through the CNM film of the device, such that a presence or amount of ionizing radiation in the environment is indicated by the current or current change.

Yet another embodiment of the invention is a method of quantifying an ionizing radiation. The method includes the steps of: exposing a device, configured as an ionizing radiation detector according to an embodiment described above, to ionizing radiation; measuring current flow through the CNM film of the device; and comparing the current to a standard curve or data set correlating changes in current to known amounts of ionizing radiation, whereby said ionizing radiation is quantified.

BRIEF DESCRIPTION OF THE DRAWINGS

FIG. 9B is a graph of change in current flow (in µA; y-axis) through the ion detector as in FIG. 9A. Increased pressure led to a higher change in the current flowing through the graphene as the ion source was turned on.

DETAILED DESCRIPTION OF THE INVENTION

The invention provides miniaturized devices capable of detecting ions in an ultrasensitive manner and having low power consumption and low cost. The devices can be used in a variety of applications, including biomedical, nuclear, vacuum, aerospace, radioactive material detection, medical radiation monitoring, electron/ion beam calibration, pressure monitoring, hazardous gas detection, and for detection of energetic particles in outer space.

Figure 2B:
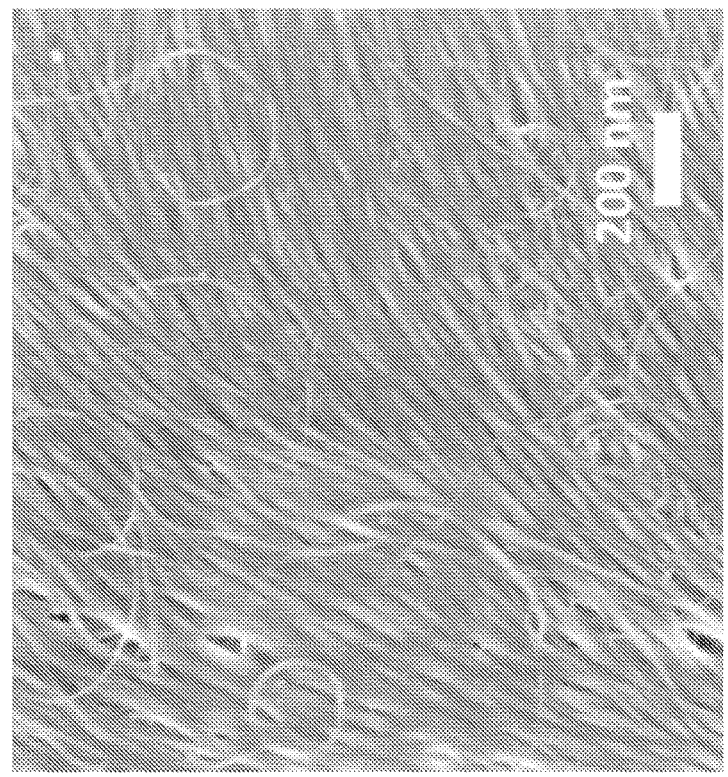
FIG. 2B is a scanning electron microscope (SEM) image of carbon nanotubes.
Figure 2A:
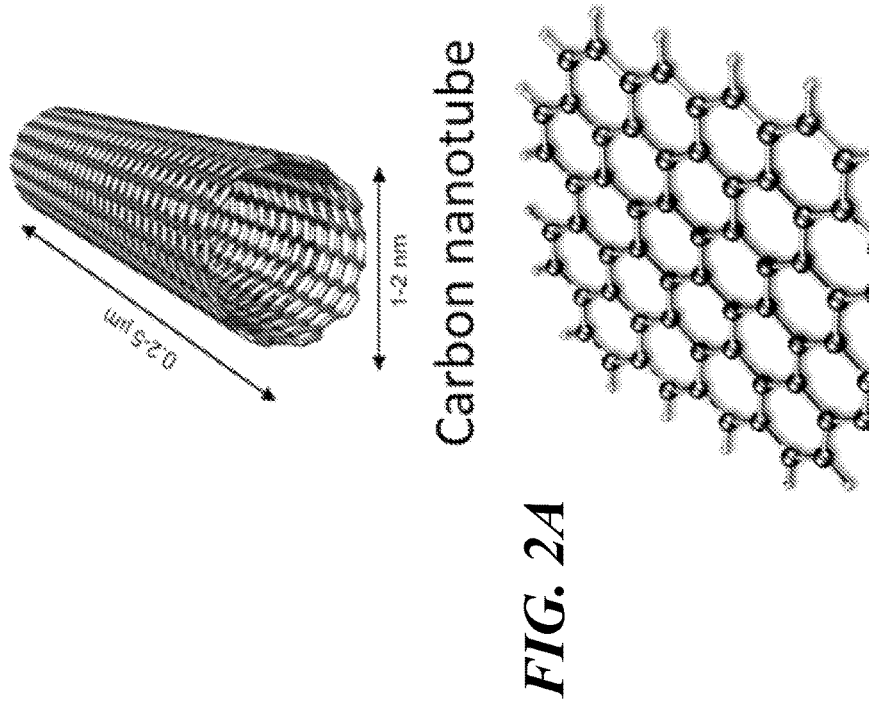
FIG. 2A is a schematic diagram of a carbon nanotube and graphene.

Provided here is a device for ultrasensitive detection of ions that detects a change in current flowing through a carbon based nanomaterial (CNM) whose resistivity changes upon the adsorption of ions. Also provided are methods of fabricating and using the device. The device may be fabricated with a number of different CNMs, including single-walled carbon nanotubes (SWCNT, see FIGS. 2A and 2B), which can be pure metallic, semi-conducting, or mixed SWCNT, double-walled carbon nanotubes (DWCNT), multi-walled carbon nanotubes (MWCNT) and graphene (FIG. 2A). Even a single carbon nanotube, or a single atomic layer of graphene, is sufficient to serve as the CNM for the device. A plurality of nanotubes or a plurality of graphene atomic layers also can be used. Preferably the CNM is configured as a strip or band of material that is deposited onto an electrically insulating substrate material, and is attached to metallic contact pads at either end of the strip, for connection to a measuring circuit. The device is highly sensitive, with a gain factor in the range of $10^4$ to $10^7$. It has a high signal-to-noise ratio, small dimension (i.e., nanoscale or microscale), and low power consumption. The device operates to reflect real time changes in the amount or concentration of ions present, and is compatible with complementary metal oxide semiconductor (CMOS) technology.

The term "gain factor" as used herein is a measure of gain (i.e., the ratio of output signal to input signal). The gain factor can be measured, for example, as the ratio of the change in charge perceived by the ion detector in 120 seconds per unit area of the sensor, to the charge received by a Faraday cup in 120 seconds per unit aperture of the Faraday cup, in the presence of an ion source that is producing ions in the environment of both the ion detector and the Faraday cup. Thus, in general $$\text{Gain factor} = \frac{\text{Outpost signal of the ion } detecor}{\text{Input signal of the ion } detecor}$$

which can be determined as follows:

$$\text{Gain factor} = \frac{\text{Change in charge detected by ion detector in 120s ion source on}}{\text{Charge received by Faraday cup in 120s ion source on}} \times \frac{\text{Aperture of Faraday cup}}{\text{Sensing Area of ion sensor}}.$$

Since the ion detector and the Faraday cup are located adjacent to each other, they are considered to receive the same number of positive ions at any given time. Thus, the charge received by Faraday cup may be regarded as the input signal for the ion detector. Charge is equal to the time integral over the current change. The change in charge detected by the ion detector is calculated by converting the change in the current flowing through the detector to change in charge (charge=current×time). The change in charge is regarded as the output signal for the ion detector. The aperture of Faraday cup and the sensing area of the ion detector are used to calculate charge received per unit area by the Faraday cup, and the change in charge detected per unit area by the ion detector, respectively.

Figure 1A:
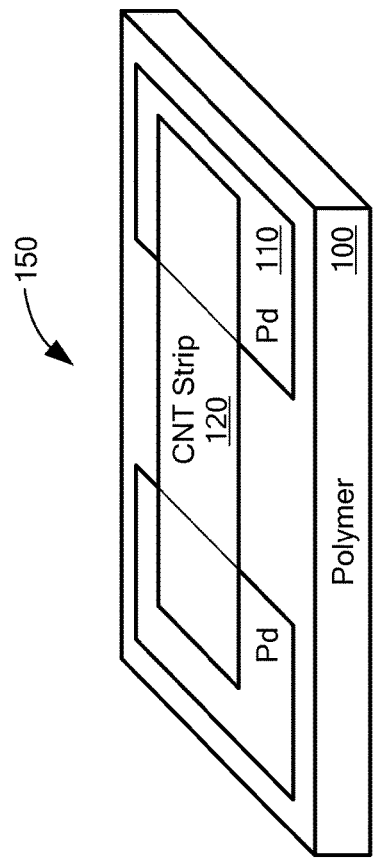
FIG. 1A is a schematic diagram of a carbon nanomaterial (CNM) based ion detector (ion sensor device 150) having a substrate (100), two metallic contact pads (110), and a CNM strip (120) (carbon nanotube (CNT) strip in this embodiment) contacting the metallic pads.
Figure 1B:
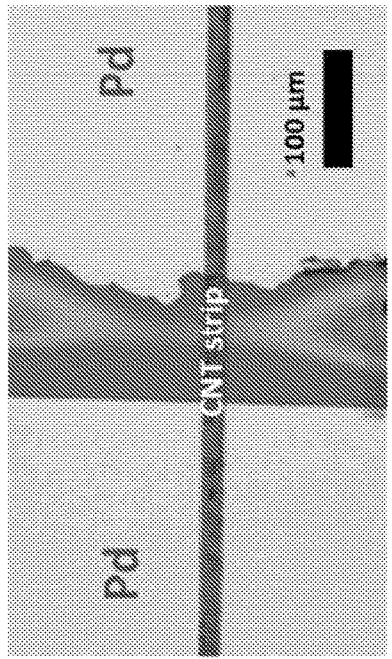
FIG. 1B is an optical image of a microscale device containing a single-walled carbon nanotube (SWCNT) strip transferred on to a substrate having Pd contact pads and in contact with the pads.
Figure 1C:
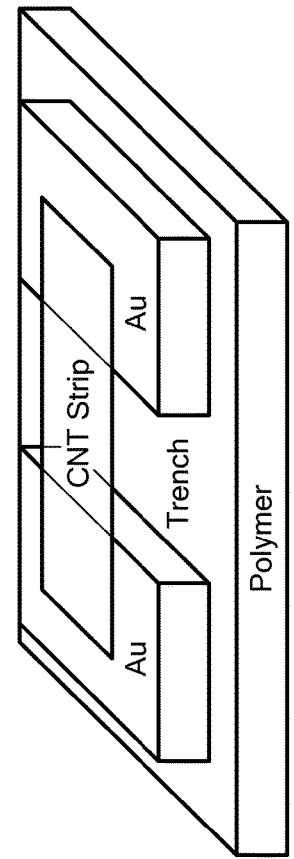
FIG. 1C is a schematic diagram of an ion detector based on a suspended carbon nanomaterial (CNM) strip having a substrate, two metallic contact pads, and a CNM strip bridging on the polymer trench and in contact with the pads.
Figure 1D:
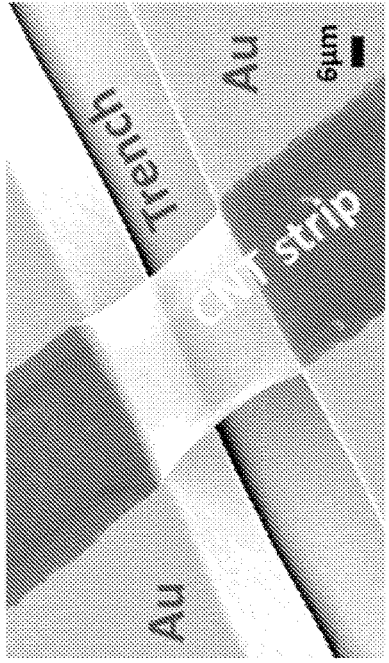
FIG. 1D is an SEM image of a microscale device of a SWCNT strip transferred to bridge on the polymer trench having Au contact pad and in contact with the pads.
Figure 1E:
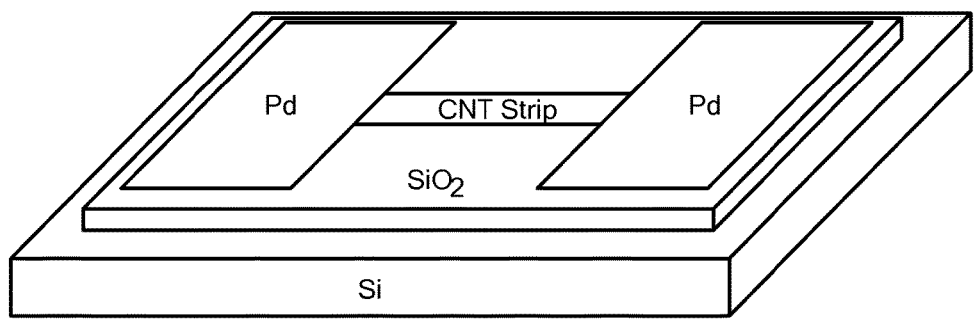
FIGS. 1E and 1F are a schematic diagram and an SEM image, respectively, of an ion sensor device in which the metallic contact pads in contact with the CNM strip are deposited on the surface of the CNM strip.
Figure 1F:
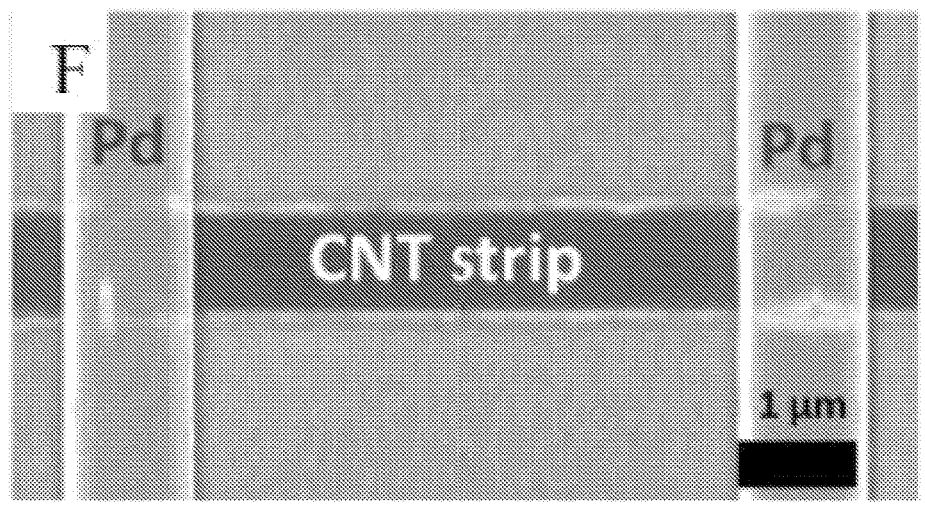
Figure 3A:
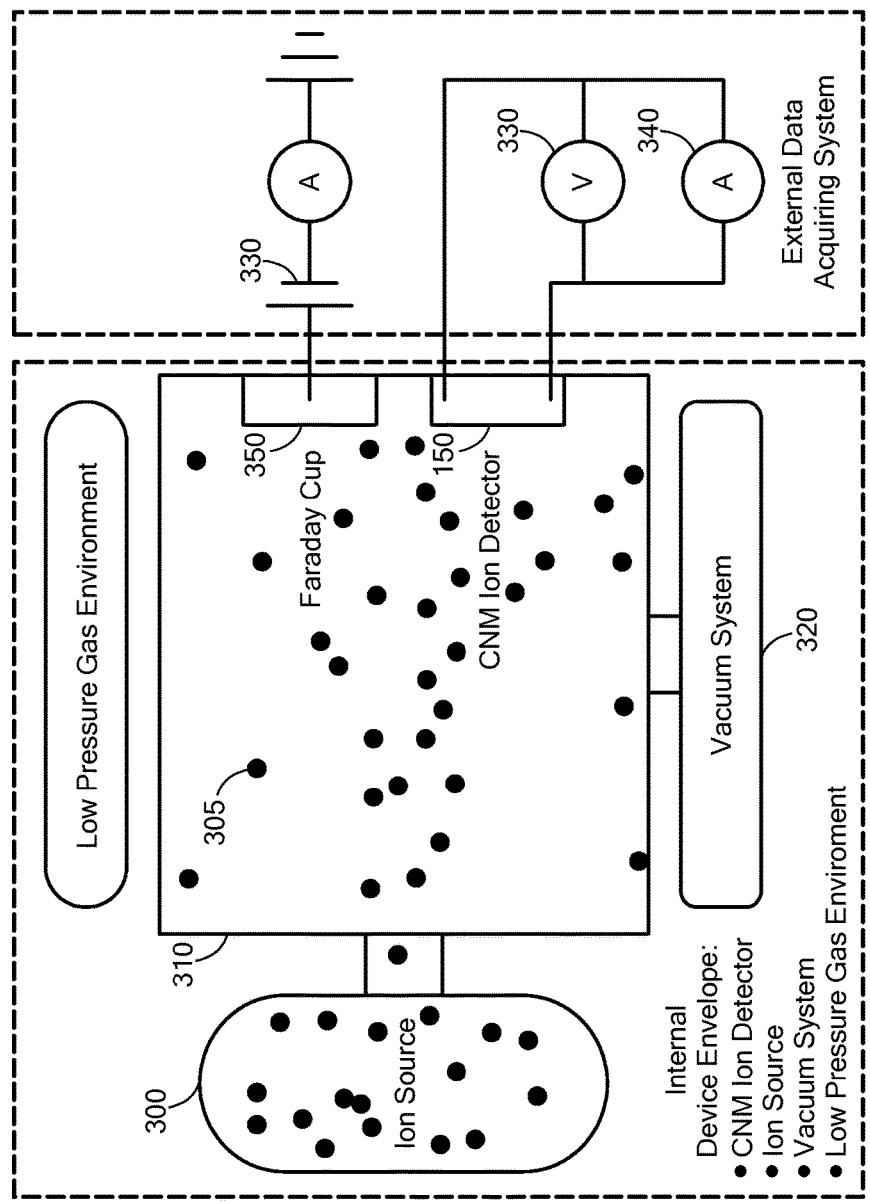
FIG. 3A is a schematic diagram of a set up for detecting ions showing an ion source (300, producing ions (305)), a vacuum chamber (310), a vacuum pumping system (320), a power source (330), an amperometry circuit (340), and a Faraday cup (350) placed within the chamber for comparison.
Figure 3B:
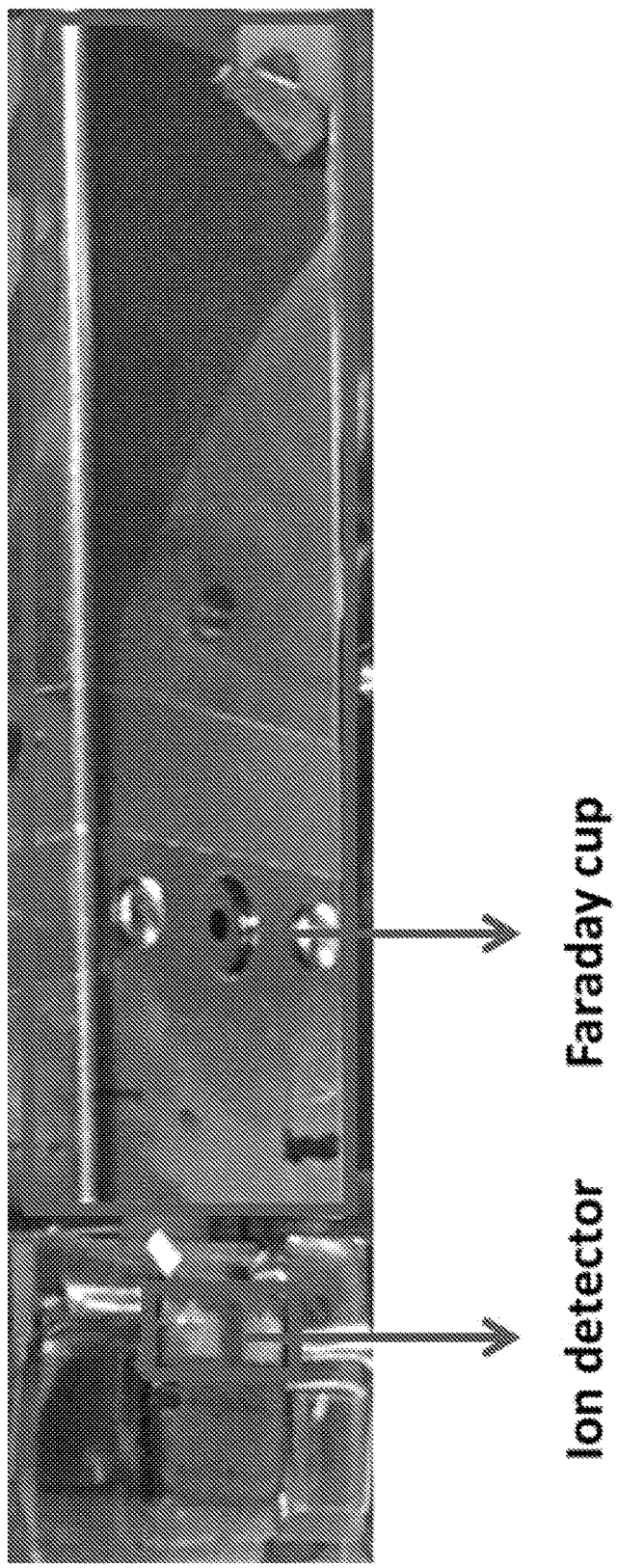
FIG. 3B is a photograph of an SWCNT-based ion detector and a Faraday cup placed side by side for size comparison.

A schematic diagram of an embodiment of an ultrasensitive ion detection device having two metallic contact pads (110) and a CNM strip (120) deposited on a substrate (100) is shown in FIG. 1A. In this embodiment the CNM is a strip of SWCNT whose ends are deposited over the metallic contact pads. An optical image of such a device is shown in FIG. 1B. An alternative embodiment is shown in FIGS. 1C and 1D, in which the CNM (a strip of SWCNT) is suspended over an open trench. This design exposes the CNM on both top and bottom sides, providing more surface area for adsorption of ions and potentially greater responsiveness. Yet another embodiment is shown in FIGS. 1E and 1F. In this embodiment, an SWCNT strip is first deposited onto the substrate, and contact pads are then deposited over the ends of the strip and also overlapping the strip ends and contacting the substrate. A photograph of a commercially available Faraday cup (FC-70) sold by Kimball Physics, Inc. (N.H., USA) is shown in FIG. 3B.

The CNM used in the device may be patterned to produce films that are microscale to nanoscale in width by choosing the appropriate method of assembly, deposition and etching. The device with two metallic contact pads and one sensing unit can be either directly assembled on a chosen substrate, or the sensing strip can be transferred to a target substrate outfitted with suitable contact pads. The contact pads can be formed of any suitable conductive metal, such as Ti, Au, Pd, or alloys thereof. The contact pads may be deposited onto the substrate either before or after transfer, assembly, or growth of CNM on the substrate. The schematic diagram in FIG. 1E shows a configuration of the device in which the metallic contact pads are deposited on top of the CNM strip. Transfer of an assembled and patterned CNM onto a target substrate has been described by Li, et al. (2011). Measurements carried out using the device have shown that the contact pads may be placed either on the CNM film or under the CNM film.

A wide range of insulating substrates may be used in the ion detector device. The substrate can contain, or be fabricated entirely from either a rigid material such as Si, $SiO_2$, or a combination thereof, or it can use a flexible polymer such as polydimethylsiloxane (PDMS), SU-8 photoresist (a type of epoxy resin), or poly(methyl methacrylate) (PMMA). Polymer materials that are used as photoresists in photolithography or e-beam lithography can also be used as substrate material, including AZ® nLOF™ 2000 series photoresists and MICROPOSIT S1800 series photoresists. A preferred form for the substrate is any three-dimensional solid with at least one face that is substantially planar in the area where the ion detector device is fabricated; however, the form of the substrate can be any form determined by the user.

The device can be used as part of a system to measure vacuum within a sealed chamber by detecting ions present in the chamber. Such a system is shown schematically in FIG. 3A and in real form in FIG. 3B. A Faraday cup is placed as a control. The sealed chamber has an ion source, and an access to a pump for evacuating the chamber in a controlled manner to maintain a desired level of pressure within the sealed chamber. The system includes a power source and an ammeter. In such a system, the ion detector device of the present invention can replace a Faraday cup which is often used in such systems. Thus, the invention contemplates a system for measuring low pressure or vacuum, the system including the ion detector, an ion source, a sealed chamber, and a gas at low pressure within the chamber. The system optionally can include a pump for reducing the pressure or establishing a vacuum within the chamber and/or electronics used in conjunction with the ion detector, such as a power supply and/or monitoring electronics, optionally including a wireless transmitter.

Ions detected by a device of the present invention can originate from an ion source device within the ion detection device or present in a system or device in which the ion detection device is installed, or can originate from the environment in which the ion detection device is placed. Ion sources are commercially available and are used, for example, in mass spectrometers and particle accelerators. Radioactive material can be a source of ions. Detectable ions include negatively or positively charged atoms or molecules of any size or charge. Positively charged ions are preferred in certain embodiments of the detector.

Figure 3C:
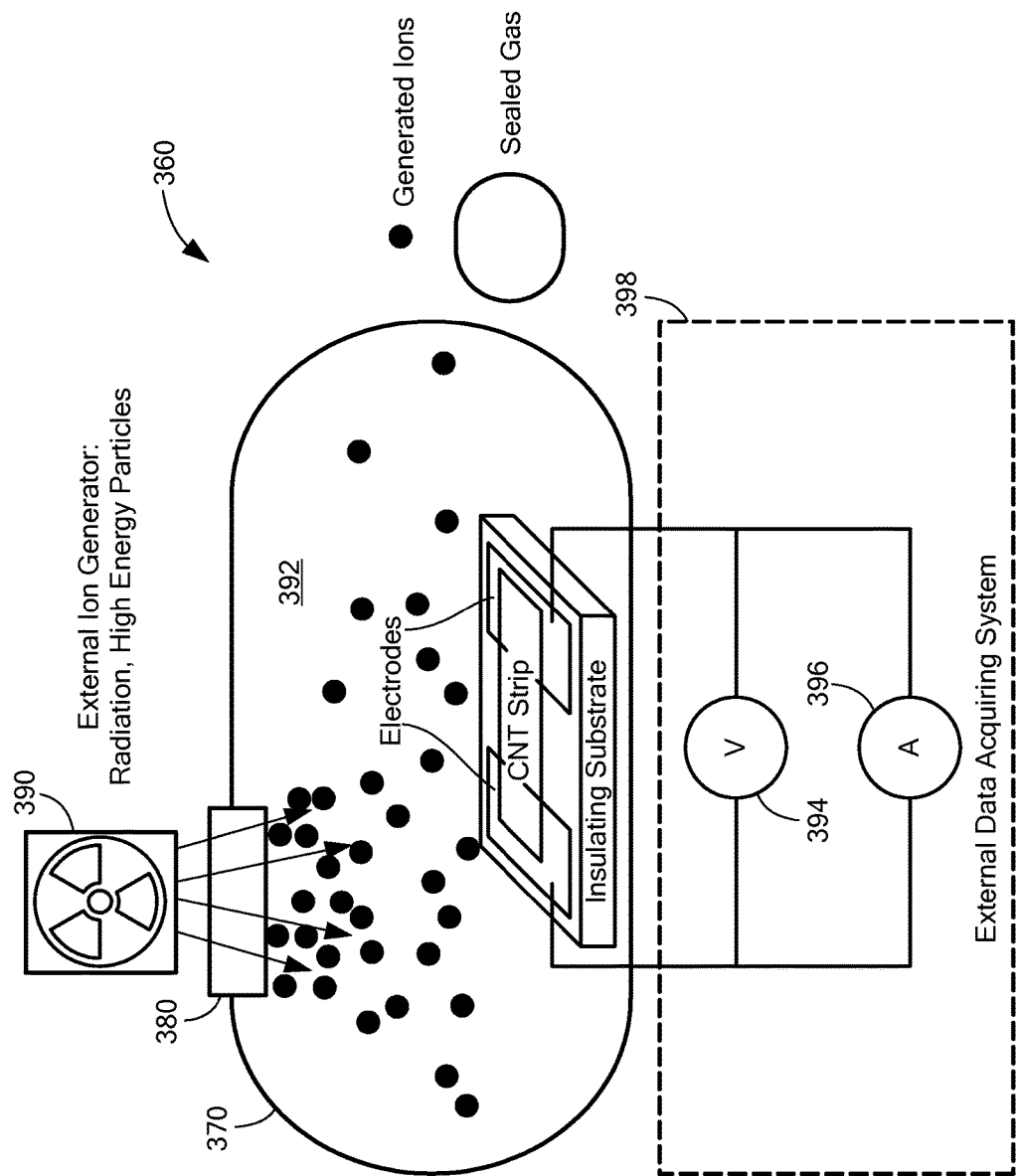
FIG. 3C is a schematic diagram of the setup of an ion detector (360) having a sealed gas chamber (370) with a window (380) to detect ions generated by external radiation or high energy particles showing an external ion generator (radiation or high energy particles (390)), a gas (392) within the sealed chamber, a power source (394), and an amperometry circuit (396). In this embodiment, the device (360) is connected to an external data acquisition system (398), which together with the ion detector forms a radiation detection system. Alternatively, the data acquisition system could be incorporated into the ion detector.

An embodiment of the present invention is a radiation detection device. A diagram of such a device is presented in FIG. 3C. In this embodiment, the ion detection device described above, using a CNM sensor strip attached to two metallic contact pads, is disposed within a sealed chamber filled with a gas that is initially substantially ion-free or has a low ion content, such that the CNM sensor is essentially devoid of adsorbed ions. The chamber preferably has a window that allows ionizing radiation to enter the chamber, whereupon the gas in the chamber becomes ionized by the radiation. The amount of external radiation is detected as a change in current through the CNM which is determined by the amount of ions, and therefore by the amount of radiation in the environment of the detector. The current can be output through contacts or a connector on the chamber housing, or can be wirelessly transmitted to a monitoring station. The device can include electronics for monitoring and/or transmission, or can be connected to an external device for these functions.

The ion detector device of the present invention is believed to operate through adsorption of ions to the CNM sensor of the device. Over time, or under conditions where exposed to high concentrations of ions, the sensor could become saturated with ions. In that case, the sensor can be recharged by allowing ions to dissociate over time, or by applying a reverse bias to the contact pads so as to dissociate the ions.

Figure 4A:
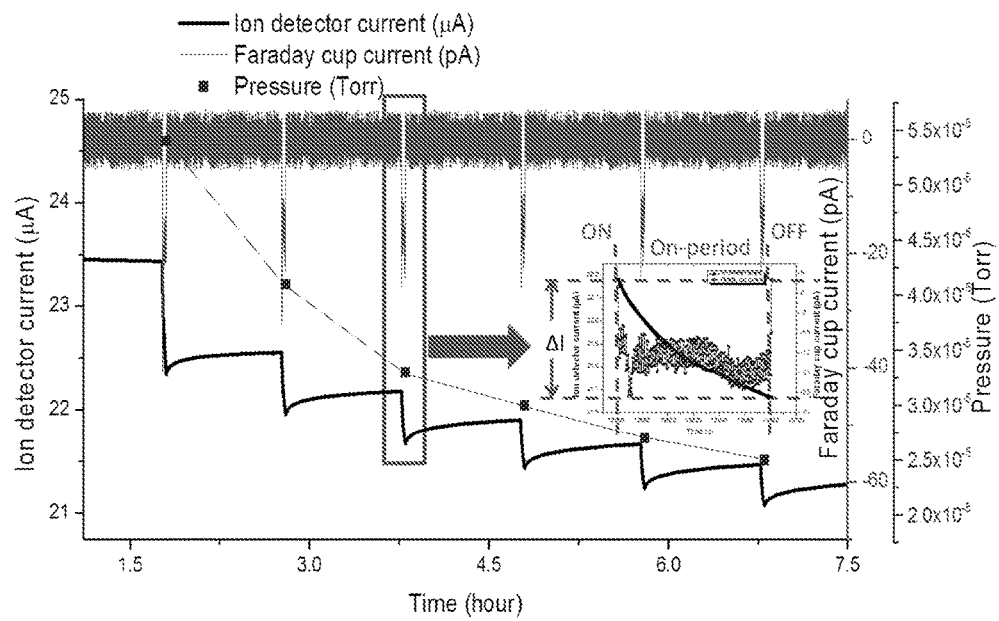
FIG. 4A is a graph of variation in the flow of current through an exemplary ion sensor device as a function of time, at varying pressure, and as the ion source was turned on and off. Pressure was recorded independently, and is shown along the y-axis on the right. The top of the graph shows the current in picoamperes (pA) flowing through the Faraday cup. A potential difference of 0.2 V was applied for measuring the current flow. The graph shows a drop in the current flow each time the ion source is turned on. The drop continues until the ion source is turned off. Change in the magnitude of current ($\Delta I$) defines the absolute value of the overall current drop during the "on-period" (2 minutes). Inset shows an enlarged view of one CNM ion sensor current change and Faraday cup current change.
Figure 4B:
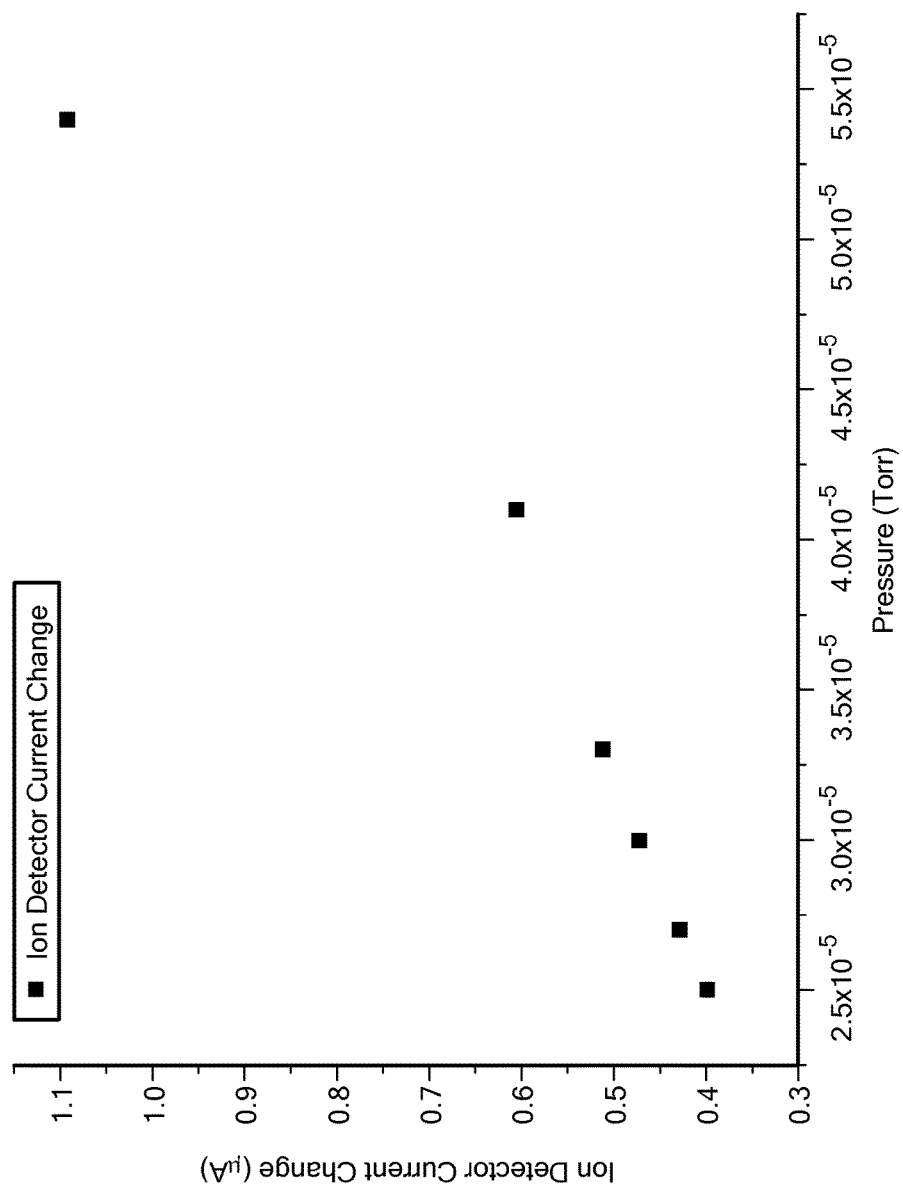
FIG. 4B is a graph correlating the variation in change in the magnitude of current, during an on-period, as a function of pressure.

Results of ion detection using the device described above is shown in FIG. 4 and FIG. 6. A sharp drop in the flow of current through the device was observed as the ion source was turned on. The magnitude of the drop is dependent on the pressure within the sealed chamber (FIG. 4A). Pressure, recorded independently, is shown along the y-axis on the right. The top of the graph shows current in picoamperes (pA) flowing through the Faraday cup. A potential difference of 0.2 V was applied for the measurements shown in FIG. 4A. Once the ion source is turned off, the sharp drop in the current flow ends. During the off period the current flow continues to drop gradually. The absolute value of the overall current drop during the "on-period" (2 minutes) is shown as ΔI in the inset. FIG. 4B shows variation in (i) the change in the magnitude of current during an on period as a function of pressure.

A similar set of measurements for detecting ions is shown in FIG. 6. A potential difference of 0.2 V was applied for the measurement. Without being limited by any theory or mechanism of action, it is considered that the gradual increase observed in the ion sensor current during the "off period" is due to ions released from the carbon nanotubes. For comparison FIG. 6A shows current measured by a Faraday cup under the same conditions of pressure and ion concentration. The Faraday cup measures far less current, and the measurement is accompanied by much noise.

Figure 6A:
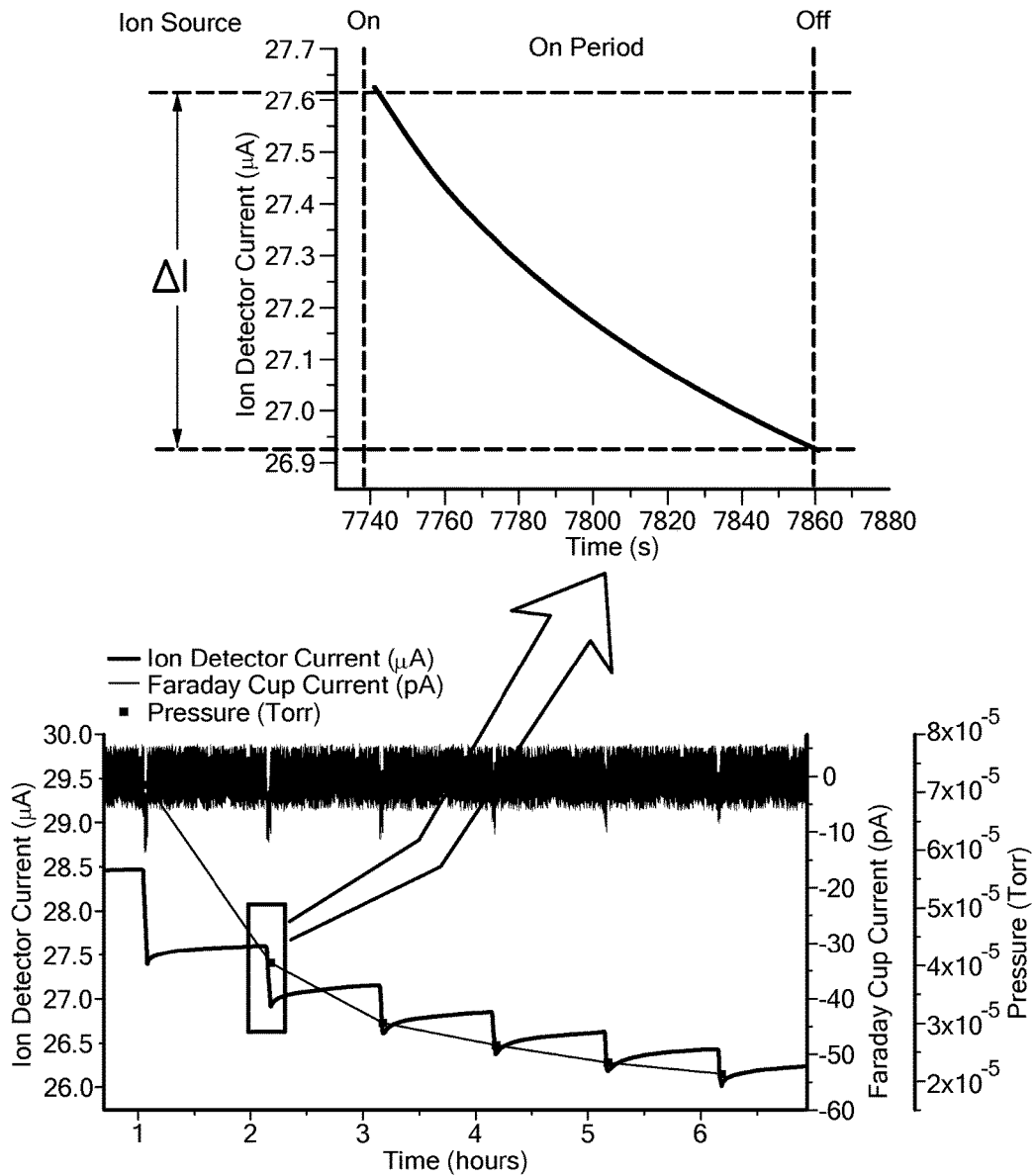
FIG. 6A is a graph of variation in the current flow (in µA; y-axis) through the CNM of an ion sensor device as a function of time (x-axis) at different pressures, as the ion source was turned on and off. Pressure was recorded independently, and is shown along the y-axis on the right. A potential difference of 0.2V was applied for measuring the current flow. The top of the graph shows the current in picoamperes (pA) flowing through the Faraday cup. The current flowing through the Faraday cup for the same value of pressure and the same amount of ions as through the CNM containing device, was much lower for the Faraday cup. Inset shows an enlarged view of one current drop.
Figure 6B:
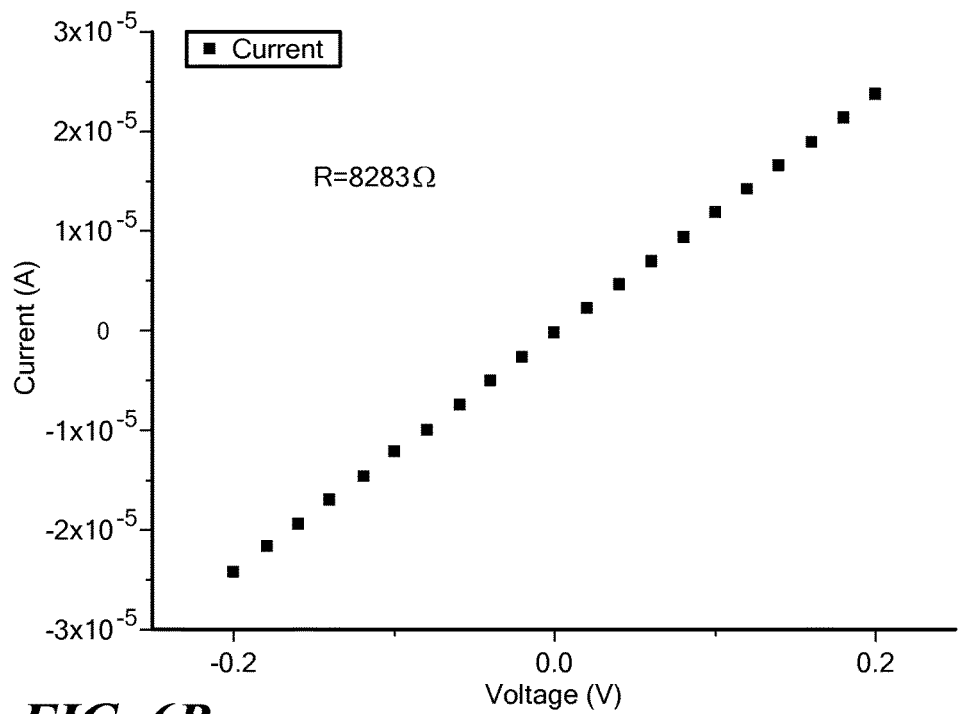
FIG. 6B is a graph of current flowing through the device as a function of voltage. Higher voltage is required for increasing the current flow. The various parameters of the measurement were: applied voltage 0.2V; ion sensor resistance 8283Ω; power of ion sensor: $5 \times 10^{-6}$ W ($P=U^2/R$)
Figure 6C:
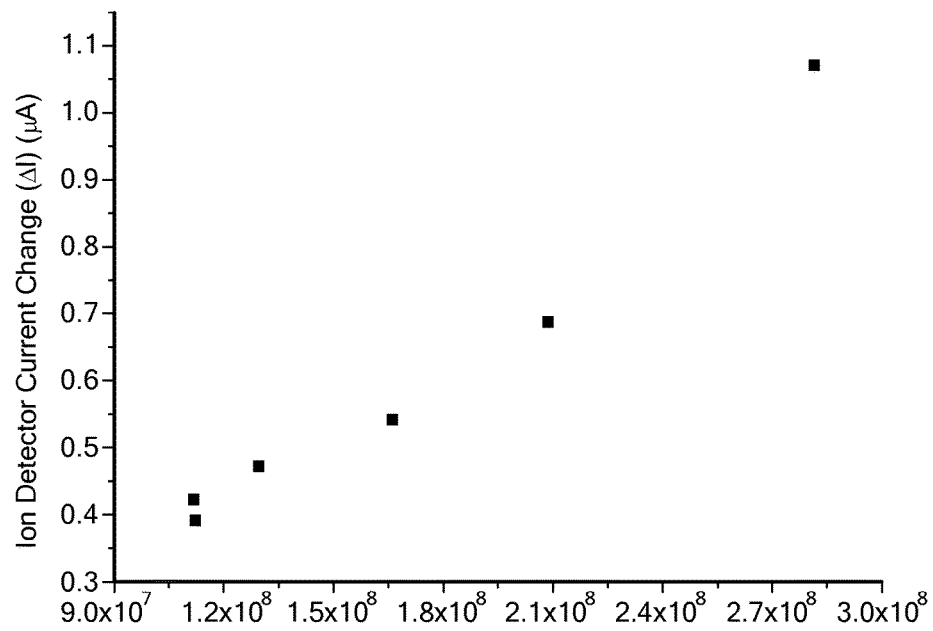
FIG. 6C is a graph of variation in the change in current flowing through a CNM strip containing device for detecting ions (FIG. 6A), measured as a function of the number of ions present in the chamber (FIG. 2E). The area of the CNM strip is 0.1 mm$^2$, and the voltage applied was 0.2 V. Increased current was observed with higher number of ions. The ion sensor device was placed 22.8 inches from the ion source.

The current change registered by the ion detector described herein increases with an increase in the number of ions exposed to the CNM of the detector (see, e.g., FIG. 6C).

Figure 6D:
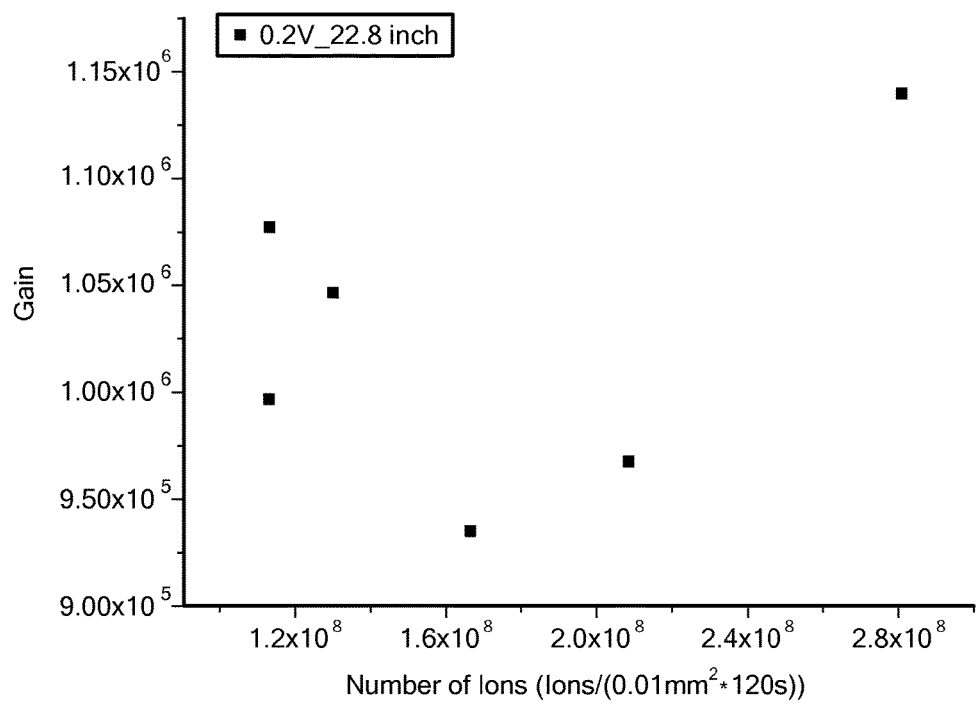
FIG. 6D is a graph of variation in the gain factor of the ion detector as a function of the number of ions present in the chamber of a device in which the ion source was separated from the CNM film (or the Faraday cup control) by 22.8 inches. With increased separation fewer ions reached the ion detector device.
Figure 7A:
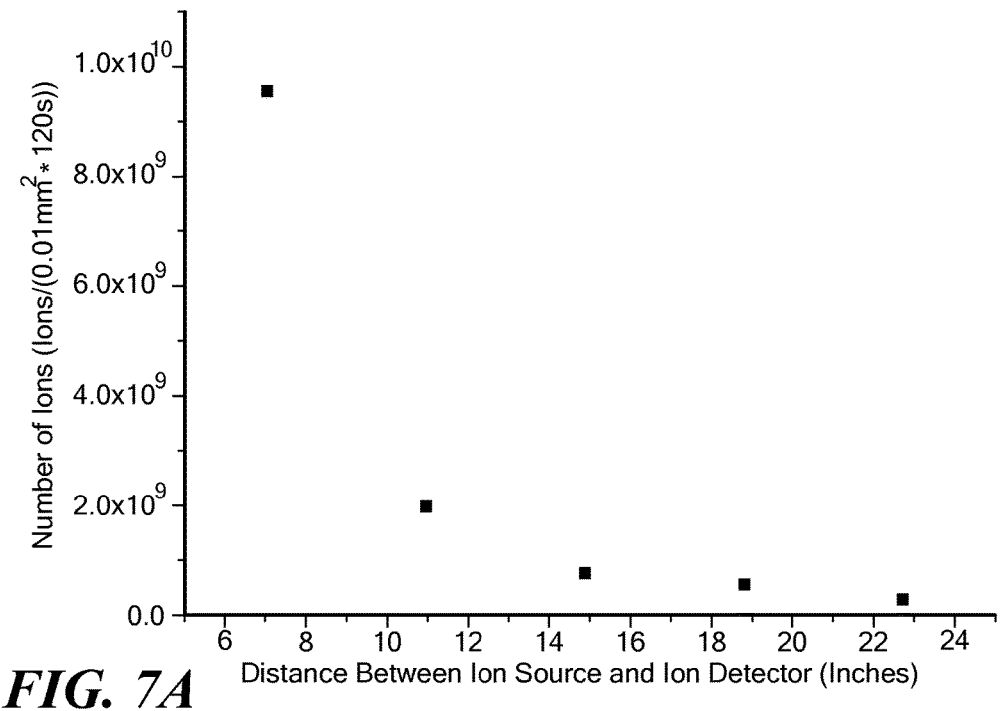
FIG. 7A is a graph of the variation in the number of ions as a function of distance between the ion source and the CNM film (or Faraday cup) in the chamber (chamber shown in FIG. 3A). With increased distance, fewer ions reach the ion detector (or Faraday cup).
Figure 7B:
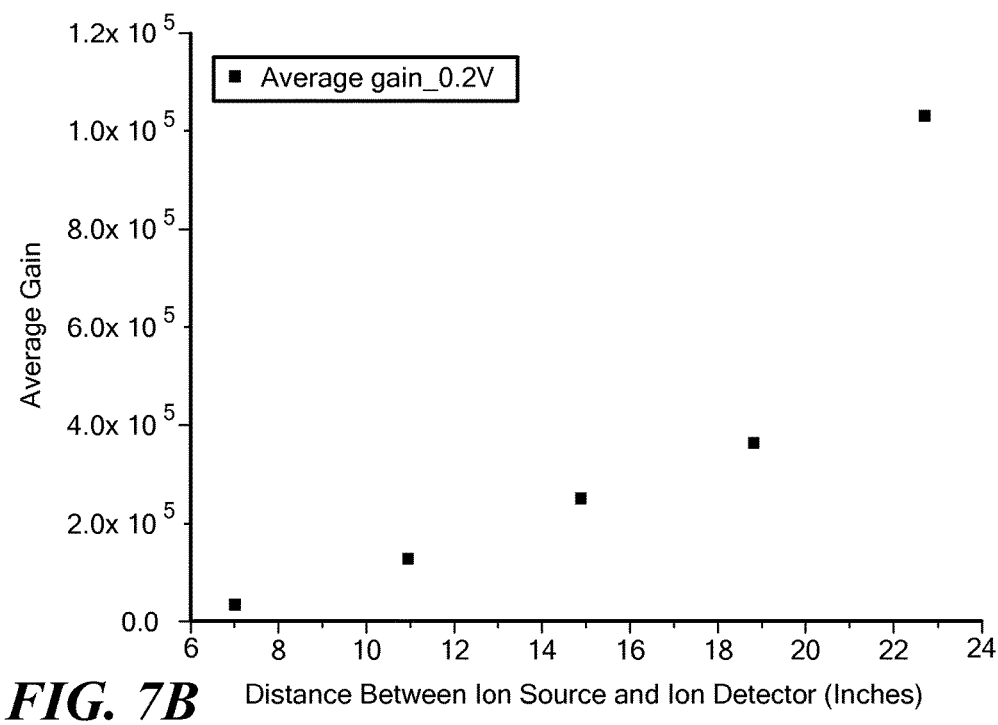
FIG. 7B is a graph of the variation in the gain factor of the ion detector as a function of distance between ion source and the CNM film (or the Faraday cup). With fewer ions reaching the ion detector, the gain factor increases.
Figure 7C:
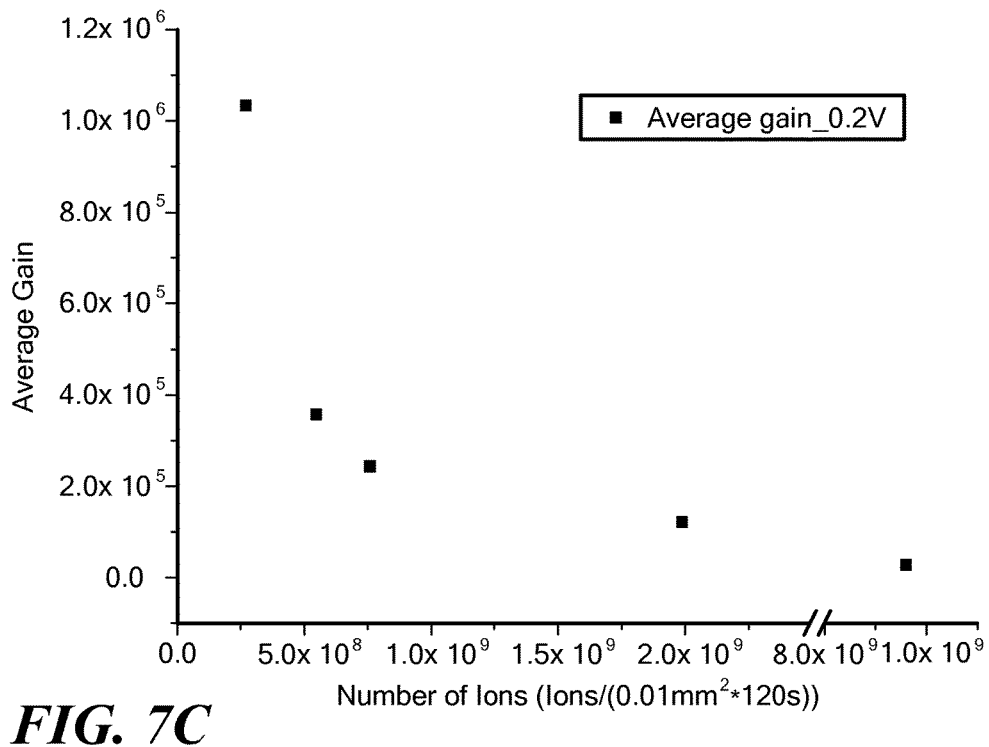
FIG. 7C is a graph of the variation in the gain factor of the ion detector as a function of the number of ions.
Figure 7D:
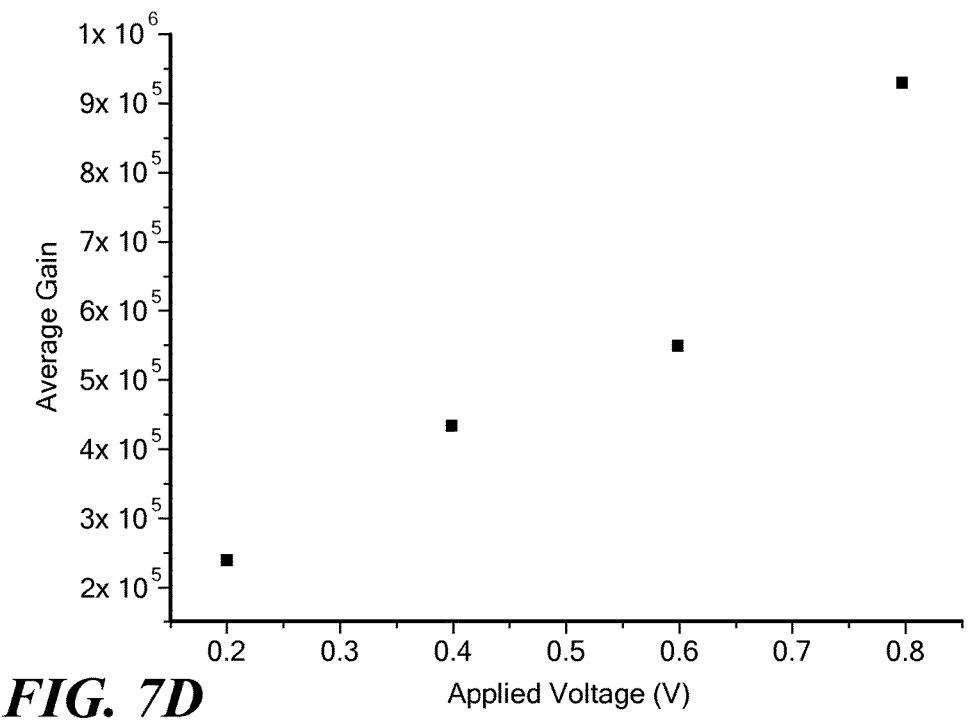
FIG. 7D is a graph of the variation in the average gain of the ion detector as a function of the applied voltage. With higher applied voltage, the average gain increases.

FIG. 6D shows gain factors (y-axis) calculated for ion detector measurements at different amounts of ions in the chamber (x-axis) when the Faraday cup was located at a distance of 22.8 inches from the ion source. The gain factor values for the ion detector device for measurements corresponding to FIG. 6D are shown in Table 1. The average gain factor for ion detector devices of the present invention, located 22.8 inches from the ion source, was determined to be $1.03 \times 10^6$. The average gain at 0.2V as a function of distance between the ion source and ion sensor (or Faraday cup) are shown in FIG. 7B, and the average gain as a function of the number of ions at 0.2V and 14.91 inches distance are shown in FIG. 7C.

TABLE 1

Gain factor of ion detector device located 22.8 inches away from the ion source.

| Measurement ID | Charge received by ion detector (C) | Charge received by Faraday cup (C) | Gain |
| --- | --- | --- | --- |
| 1 | $5.12 \times 10^{-5}$ | $8.99 \times 10^{-10}$ | $1.14 \times 10^6$ |
| 2 | $3.23 \times 10^{-5}$ | $6.68 \times 10^{-10}$ | $0.97 \times 10^6$ |
| 3 | $2.49 \times 10^{-5}$ | $5.33 \times 10^{-10}$ | $0.93 \times 10^6$ |
| 4 | $2.18 \times 10^{-5}$ | $4.17 \times 10^{-10}$ | $1.05 \times 10^6$ |
| 5 | $1.95 \times 10^{-5}$ | $3.62 \times 10^{-10}$ | $1.08 \times 10^6$ |
| 6 | $1.81 \times 10^{-5}$ | $3.63 \times 10^{-10}$ | $0.99 \times 10^6$ |

The signal to noise ratio obtained with the ion detector described herein is much greater than that obtained with a Faraday cup. Signal-to-noise ratio (SNR) is calculated as a ratio of average current change to the noise in measurement.

$$SNR = \frac{\text{Average current change}}{\text{Noise}}$$

Figure 8A:
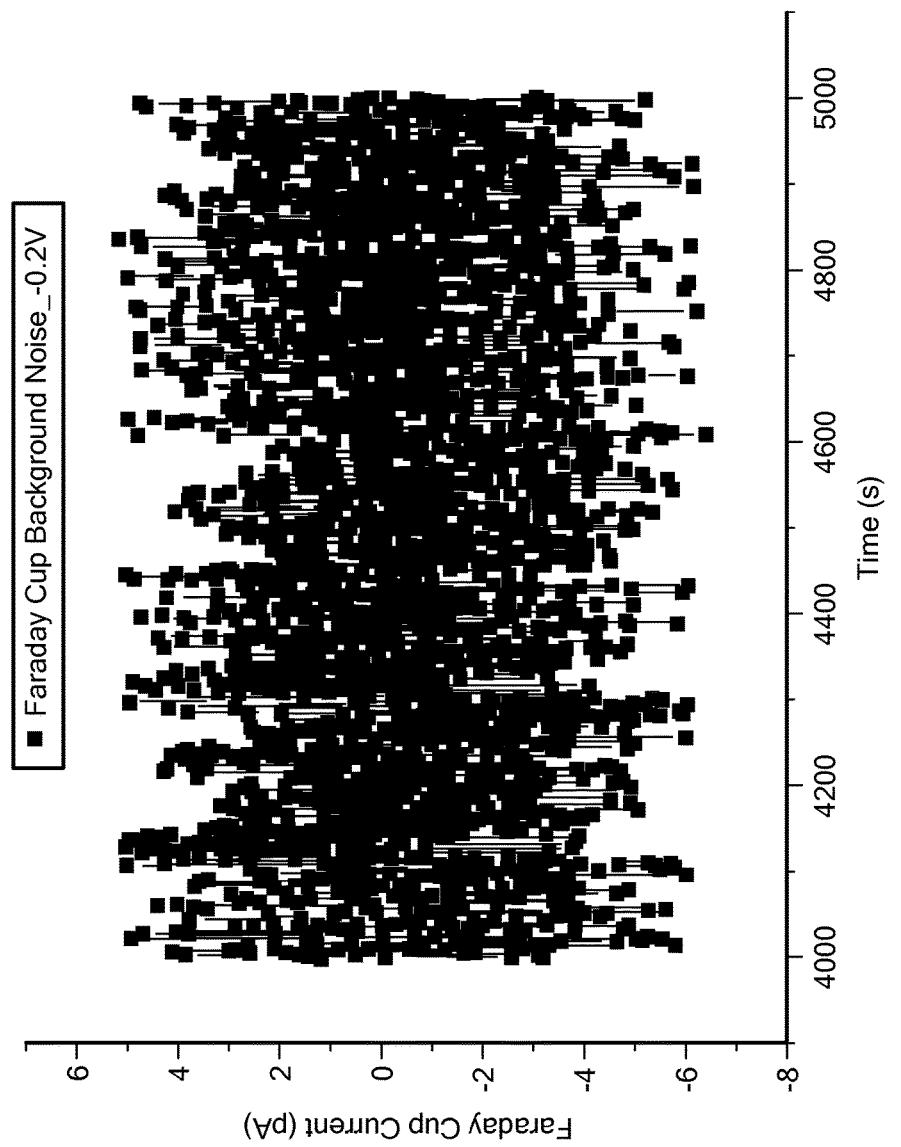
FIG. 8A is a graph of the background current detected by a Faraday cup at −0.2 V as a function of time.

For a Faraday cup, average current change is measured by the ratio of the charge received by the Faraday cup to the time the ion source was "on" (120 seconds). FIG. 8A is a graph showing a typical pattern of background current measured by the Faraday cup at −0.2V as a function of time. The background noise of the Faraday cup did not appreciably change with pressure. The noise of measurement was estimated to be about 11.5 pA. Thus, $$\text{Average current change(Faraday cup)} = \frac{\text{charge received by Faraday cup}}{120s}$$

SNR values for measurements corresponding to FIG. 6D were calculated according to the relationship above and are shown in Table 2.

TABLE 2

SNR of Faraday cup located 22.8 inches away from the ion source.

| Measurement ID | Average current change of Faraday cup (pA) | SNR |
| --- | --- | --- |
| 1 | 7.49 | 0.65 |
| 2 | 5.56 | 0.48 |
| 3 | 4.44 | 0.39 |
| 4 | 3.47 | 0.30 |
| 5 | 3.01 | 0.26 |
| 6 | 3.02 | 0.26 |

The results show that at low ion numbers, and for a distance of 22.8 inches, the SNR for the Faraday cup was in the range of 0.26-0.65. This value of SNR is so low that the signal cannot be detected reliably.

Figure 8B:
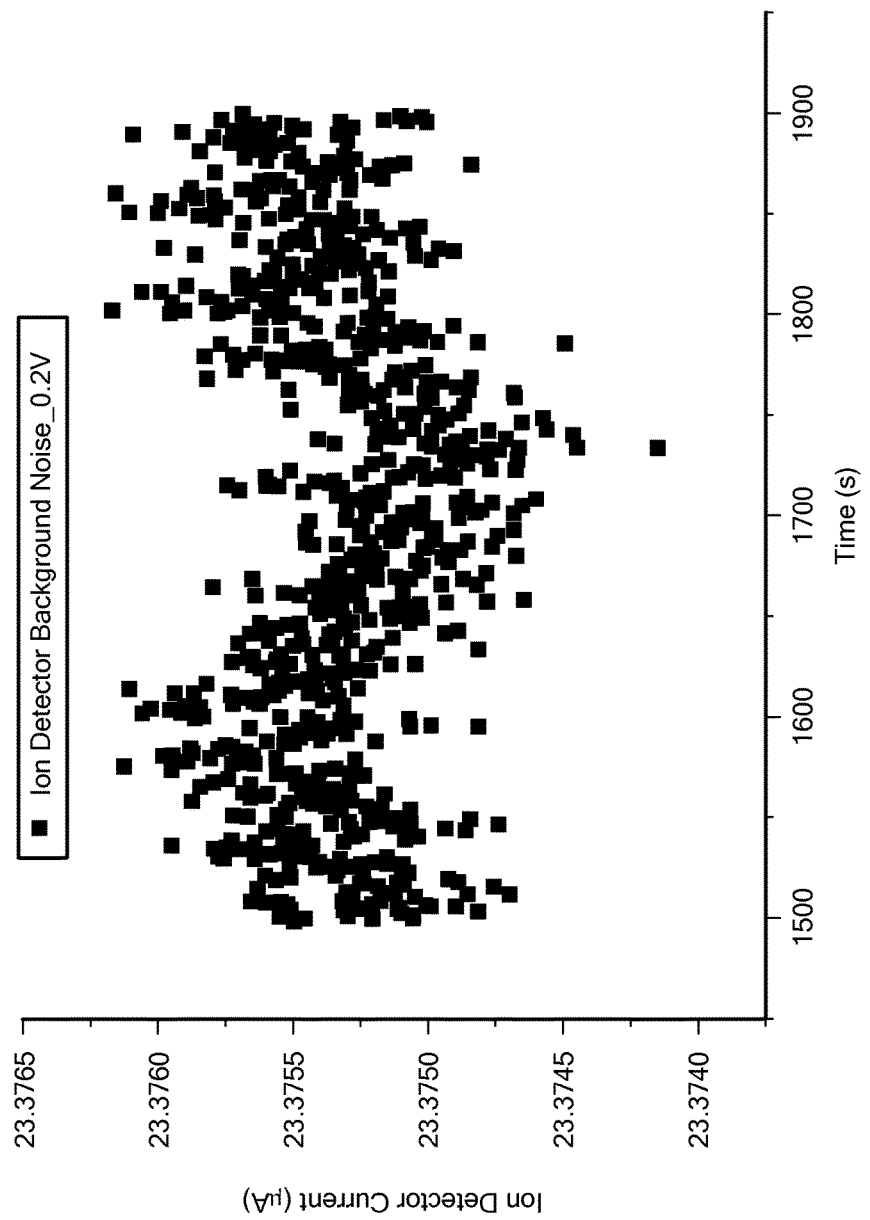
FIG. 8B is a graph of the background current detected by a CNM film-containing ion detector device as a function of time at 0.2V.
Figure 9A:
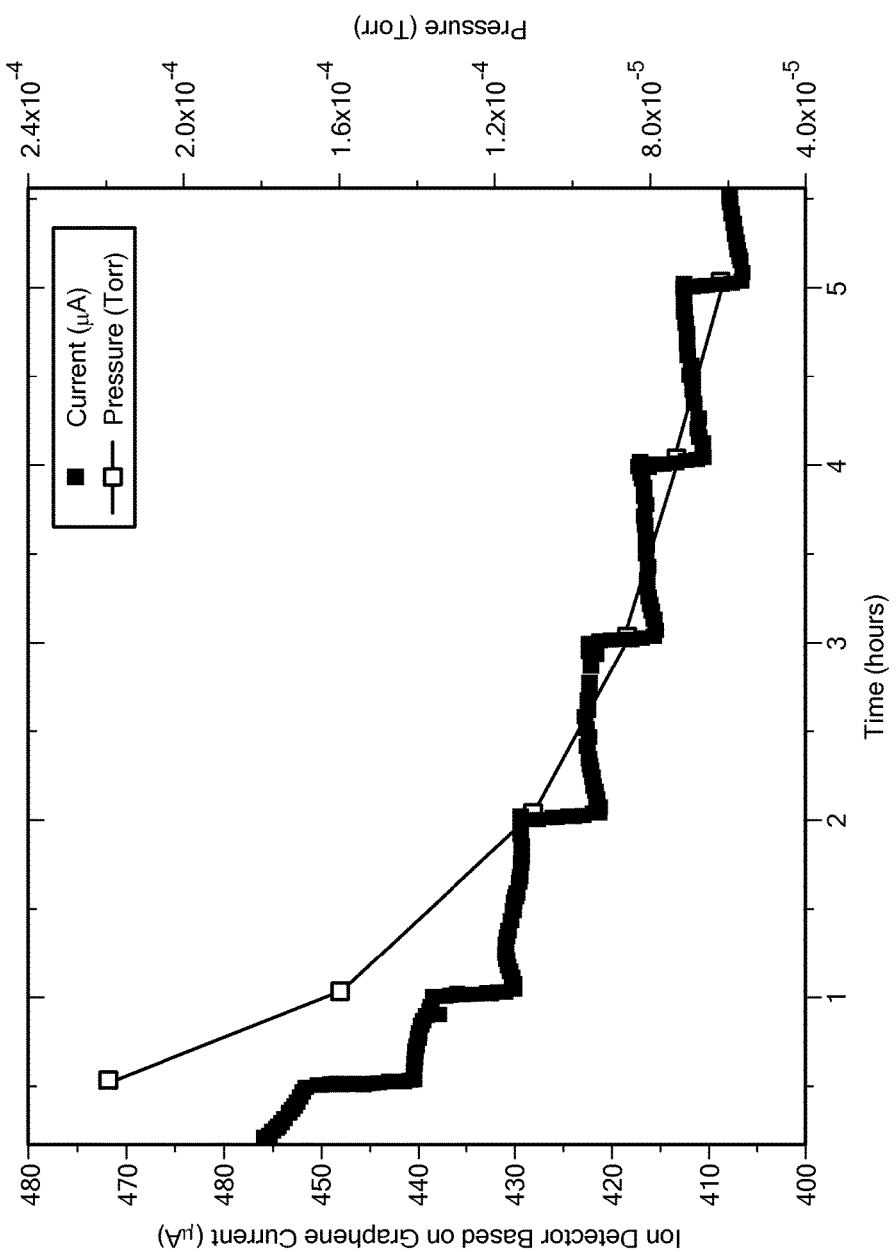
FIG. 9A is a graph of variation in the current (in µA; y-axis) flowing through an ion detector having a CNM film of graphene, measured as a function of time (x-axis), and at different pressures, as the ion source was turned on and off. Pressure was recorded independently, and is shown along the Y-axis on the right. A potential difference of 0.1 V was applied.
Figure 9B:
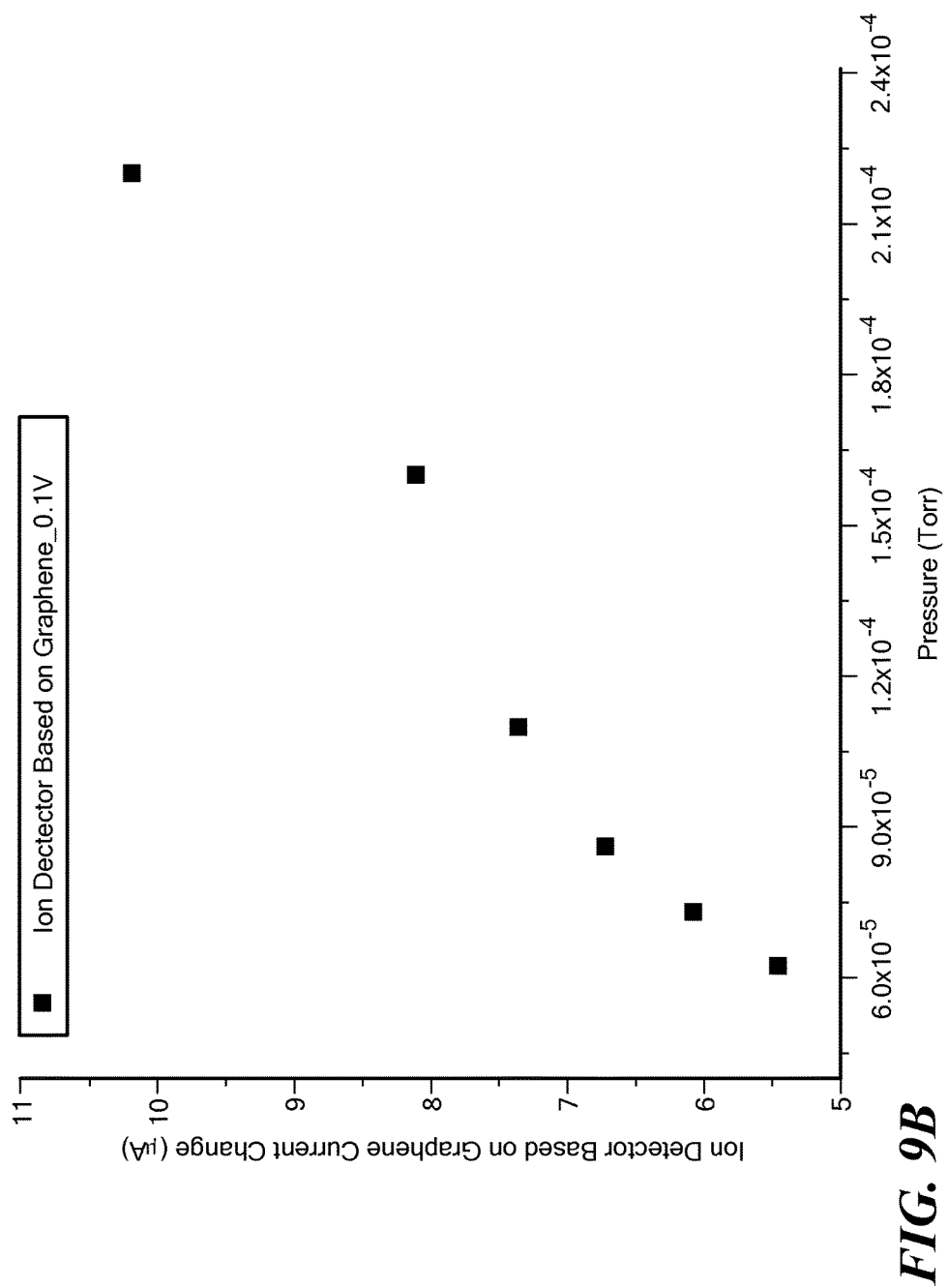

For the ion detector device described herein, the noise was observed to be about 1.5 nA. See, e.g., the highest end of the range of background noise in FIG. 8B. The current flowing through the device was in the range of 23.3745 to 23.3760 µA (FIG. 8B). The SNR values for the ion detector device for measurements corresponding to FIG. 6D, were calculated and are shown in Table 3.

TABLE 3

SNR of ion detector device located 22.8 inches from the ion source.

| Measurement ID | Average current change of ion detector (nA) | SNR |
| --- | --- | --- |
| 1 | 426.5 | 284.4 |
| 2 | 269 | 179.3 |
| 3 | 207.5 | 138.4 |
| 4 | 181.6 | 121.1 |
| 5 | 162.3 | 108.2 |
| 6 | 150.5 | 100.3 |

Comparison of the data in Table 2 and Table 3 shows that the ion detector device described herein has a much greater SNR ratio.

A comparison of the detection limits of the Faraday cup and the ion sensor shows that the ion detector device of the present invention has much greater sensitivity.

For calculating detection limits it is assumed that one positive ion carries one elementary charge.

1 elementary charge = $1.6 \times 10^{-19}$ C, hence 1 ion = $1.6 \times 10^{-19}$ C 1 ion/second = $1.6 \times 10^{-19}$ C/s, Since current = $\frac{charge}{time}$, 1 ion/s = $1.6 \times 10^{-7}$ pA.

Ion detector detection limit = $\frac{\text{Noise of ion sensor}}{\text{Gain} \times 1 \text{ ion/s}}$ For the Faraday cup, gain is about 1, and the noise is about 11.5 pA, so the detection limit is Detection limit = $\frac{\text{Noise}}{1.6 \times 10^{-7} \text{ pA}} = \frac{11.5 \text{ pA}}{1.6 \times 10^{-7} \text{ pA}} = 7.2 \times 10^7$ ions/s For the ion sensor at 22.8 inches, the gain is about 10, and the noise is about 1.5 nA. Therefore, the detection limit is $\frac{1.5 \text{ nA}}{10^6 \times 1.6 \times 10^{-7} \text{ pA}} = 9375$ ions/s The invention having now been fully described, it is exemplified by the following examples and claims which are for illustrative purposes only and are not meant to be further limiting.

EXAMPLES

Example 1: Fabrication of a Microscale Miniaturized Ion Detector Using Carbon-Based Nanomaterials A Si/SiO$_2$ substrate (SiO$_2$ layered on to Si) of about 400 nm thickness was pretreated with inductively coupled plasma using a mixed gas flow of O$_2$ (20 sccm), SF$_6$ (20 sccm), and Ar (5 sccm). A microscale SWCNT film was assembled on the SiO$_2$/Si substrate by dip-coating the plasma treated substrate into a suspension of SWCNT in deionized water, and removing the substrate from the suspension at a constant speed (0.05 mm/min) The SWCNT strip was composed of both metallic and semi-conductive SWCNTs. A layer of photoresist (S1818, MicroChem Corp., Newton, Mass.) was spin coated on top of the SWCNT and patterned to generate strips of exposed SWCNT, each strip 20 μm in width. O$_2$ plasma was used to etch the strips of exposed SWCNT film, and after removing the photoresist, an array of SWCNT strips was obtained. An SWCNT strip was transferred using a wet-contact print method to a receiving substrate (SU-8) pre-coated with Pd contact pads (Li et al., 2011). The two contact pads were separated by a gap of 105 μm. The device had an active area for area for ion detection of about $18 \times 10^5 = 1890$ μm$^2 = 1.89 \times 10^{-3}$ mm$^2$. In comparison, a commercial Faraday cup (FC-70, from Kimball Physics, Inc. Wilton, N.H.) has an active area of 2 mm$^2$ (FIG. 3B).

In a related embodiment, a suspended device architecture was utilized to improve ion detection. A device as shown schematically in FIG. 1D was prepared using an SWCNT strip (6 μm in width) and was subsequently transferred to a gold-coated substrate having a micro-trench (6 μm in width). The suspended region of the SWCNT strip covering the trench acted as the sensing element, and a gold film isolated by the trench was used as the electrodes (i.e., contact pads) for measurement purposes. The suspended SWCNT strip provides more active area for ion detection.

Example 2: Fabrication of a Nanoscale Miniaturized Ion Detector Using Carbon Based Nanomaterials A nanoscale miniaturized ion detector having an SWCNT strip of 200 nm width is fabricated using the same general method as described above, except that the SWCNT strip is formed by the method of template-guided fluidic assembly (Kim et al., 2009). A similar device, but having a single SWCNT spanning two contact pads, is achieved by the method of guided growth (Kong et al., 1998), where metallic catalyst islands are scattered on a Si substrate, and individual SWCNT are grown bridging two isolated metallic islands through a chemical vapor deposition process forming a measurable device. Another method for obtaining a single SWCNT device is deposition after growth, where a Si substrate coated with a self-assembled monolayer terminated with —CH$_3$ groups is soaked in SWCNT/N,N-dimethylformamide solution (0.1 mg/ml) for 10 min, immediately followed by methanol rinsing and blow-drying with nitrogen (Liu et al., 1999).

Example 3: Ion Detection Using Devices Having Carbon Based Nanomaterials (CNM)

Ion detection was performed in a well-grounded and shielded chamber at room temperature (294 K) and with controlled pressure. Positive ions were generated by a hot-filament ionization generator and air was used as the gas source. Gas molecules were bombarded with accelerated electrons to generate positive ions. The electrons and negatively charged particles were terminated by applying a grid with high positive potential, and only positive ions were released from the ion generator. Pure N$_2$ and Ar were also used with similar results. The number of ions generated is proportional to the number of gas molecules, and therefore to the pressure within the ion generator. The higher the pressure the larger the number of positive ions generated.

A pump was used to gradually decrease the pressure within the shielded chamber, and the ion source was turned on and off several times to supply fresh ions. See solid squares, FIG. 4. An "on" period lasted for two minutes. Upon turning the ion source on, a sharp decrease in current was observed until the source was turned off. The downward trend of the baseline of the current flowing through the SWCNT is a result of the dependence of the current on the pressure inside the sealed chamber. The absolute values of the overall change in the magnitude of the current (ΔI) are summarized in FIG. 4B. A linear dependence with change in pressure was observed for both the change in current and the change in resistance, indicating that the device could be used to determine the number of ions present inside the sealed chamber.

Measurement with the same concentration of ions as used in the ion detector were carried out using a commercial Faraday cup (F-70, Kimball Physic Inc., Wilton, N.H.) with an Agilent 4156 precision semiconductor parameter analyzer (Agilent Technologies, Santa Clara, Calif.). For the Faraday cup, the average change in the magnitude of current at pressure $5.8 \times 10^{-5}$ Torr was observed to be $2 \times 10^{-11}$ A, but for the ion detector, the change in the magnitude was $1.1 \times 10^{-6}$ A, which is five orders of magnitude higher than the Faraday cup.

Figure 5A:
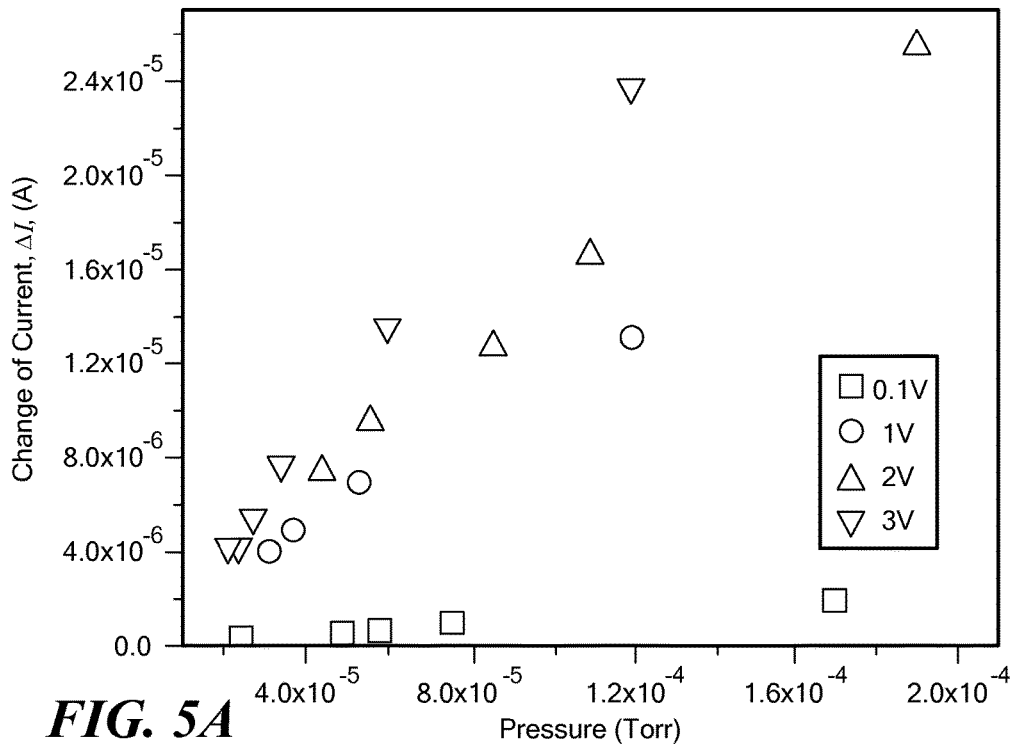
FIG. 5A is a graph of variation in the change in the magnitude of current during the "on-period" at different voltages, plotted as a function of pressure.

It was observed that the magnitude of the change in current could be amplified by increasing the applied voltage from 0.1 V to 3 V as shown in FIG. 5A. By applying a 3V bias to the device at a pressure of $1.2 \times 10^{-4}$ Torr, the magnitude of the change in current increased to $2.4 \times 10^{-5}$ A, which is at least 6 orders of magnitude higher than the signal obtained from Faraday cup.

Figure 5B:
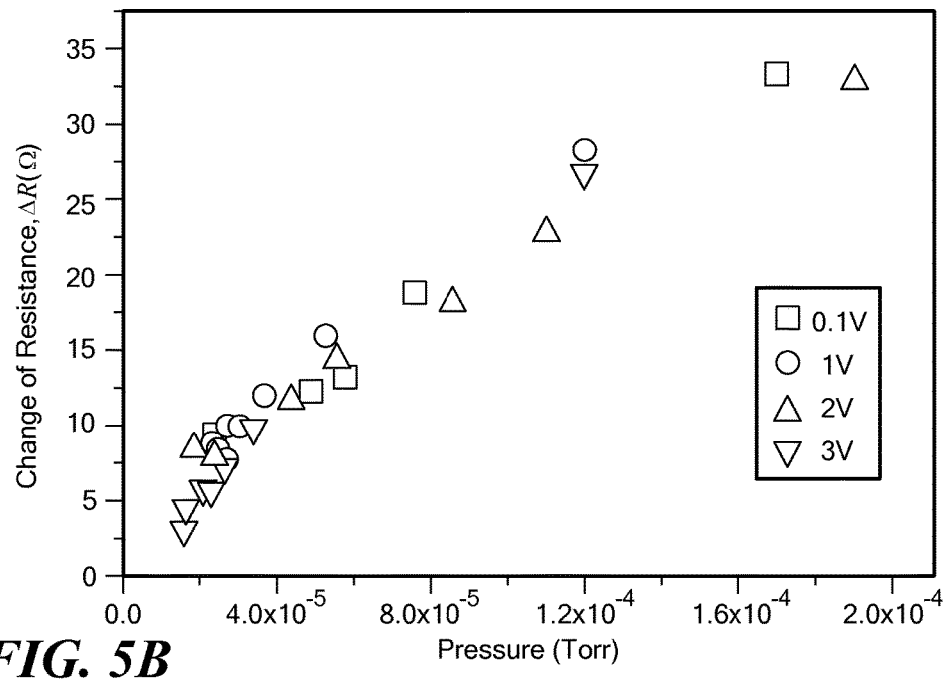
FIG. 5B is a graph of variation in the change in the resistance of the CNM film during the "on-period" at different voltages, plotted as a function of pressure.

The change in resistance was observed to remain unchanged as the applied voltage was changed (FIG. 5B), indicating that increasing the applied voltage neither enhances the interaction between SWCNT and the ions, nor does it lead to a larger number of ions interacting with SWCNT. This in turn indicates further that the SWCNT detect the ions in a passive manner. Once the ions attach to the surface of the SWCNT, the intrinsic resistance of the SWCNT changes, accompanied by a change in the output current. Applied voltage is used to tailor the output current signal, but does not change the intrinsic resistance of ion-decorated SWCNT.

This mechanism is different from the individual multi-walled carbon nanotube-based ion sensor built by Zhang et al., in which ionized $O_2^-$ applies a "built-in" potential to a carbon nanotube, leading to a change of current in the device, but not the intrinsic resistance of the carbon nano-tube (Zhang et al., 2006). Similar results were obtained with SWCNT, DWCNT, MWCNT that are pure metallic (95%) and semi-conductive (95%).

REFERENCES

Helbling, T., Drittenbass, S., Durrer, L., Roman, C., and Hierold, C., Ultrasmall single walled carbon nanotube pressure sensors, *Micro Electro Mechanical Systems*, MEMS 2009. IEEE 22nd International Conference (2009).

Kim, Y. L., Li, B., An, X., Hahm, M. G., Chen, L., Washington, M., Ajayan, P. M., Nayak, S. K., Busnaina, A., Kar, S., and Jung, Y. J., Highly aligned scalable platinum-decorated single-wall carbon nanotube arrays for nanoscale electrical interconnects, ACS Nano, 3(9), 2009, 2818-2826.

Kong, J., Soh, H. T., Cassell, A., Quate, C. F., and Dai, H., Synthesis of individual single-walled carbon nanotubes on patterned silicon wafers, Nature, 395, 1998, 878-881.

Li, B., Hahm, M. G., Jung, Kim, Y. L., H. Y., Kar, S., and Jung. Y. J., Highly organized two- and three-dimensional single-walled carbon nanotubes-polymer hybrid architectures, ACS Nano, 5 (6), 2011, 4826-4834.

Liu, J., Casavant, M. J., Cox, M., Walters, D. A., Boul, P., Lu, W., Rimberg, A. J., Smith, K. A., Colbert, D. T., and Smalley. R. E., Controlled deposition of individual single-walled carbon nanotubes on chemically functionalized templates, Chemical Physics Letters, 303(1-2), 1999, 125-129.

Ma, J., Yeow, J. T. W., Chow, J. C. L., and Barnett, R. B., A carbon nanotube-based radiation sensor, *International Journal of Robotics and Automation*, vol. 22:49-58 (2007).

Mattmann M, Roman C, Helbling T, Bechstein D, Durrer L, Pohle R, Fleischer M, Hierold C., Pulsed gate sweep strategies for hysteresis reduction in carbon nanotube transistors for low concentration $NO_2$ gas detection *Nanotechnology* 21:185501 (2010).

Modi, A., Koratkar, N., Lass, E., Wei, B., and Ajayan, P. M., Miniaturized gas ionization sensors using carbon nanotubes Nature, 424:171-174 (2003).

Stampfer, C., Jungen, A., and Hierold, C., Fabrication of discrete nanoscaled force sensors based on single-walled carbon nanotubes, *IEEE Sens. J.*, vol. 6, pp. 613-617 (2006).

Sumanasekera, G. U., Adu, C. K. W., Fang, S. and Eklund, P. C., Effects of gas adsorption and collisions on electrical transport in single-walled carbon nanotubes, *Physical Review Letters*, vol. 85, pp. 1096-1099 (2000).

Wang, Y., and Yeow, J. T. W., A review of carbon nanotube-based gas sensors, *Journal of Sensors*, vol. 2009, Article ID 493904, 1-24 (2009).

Yang, L., and J. Han, J., Electronic structure of deformed carbon nanotubes, *Phys. Rev. Lett.*, vol. 85, pp. 154-157 (2000).

Zhang, J. B., Xi, N., Chan, H., and Li, G., Single carbon nanotube based ion sensor for gas detection, *Nanotechnology*, 2006. IEEE-NANO 2006. Sixth IEEE Conference (2006).

What is claimed is:

1. An ionizing radiation detection device comprising:
an insulating substrate;
first and second metallic contact pads disposed on a surface of the substrate;
a strip of carbon-based nanomaterial (CNM) film, the strip having a first end and a second end, the first end in contact with the first pad and the second end in contact with the second pad, wherein said strip of CNM film consists of graphene or a plurality of single-walled carbon nanotubes (SWCNT); and
a sealed housing enclosing the substrate, pads, and CNM film and forming a chamber; wherein the chamber comprises a gas that becomes ionized by radiation incident on the device; and wherein a potential difference applied across the pads causes current to flow through the CNM film and ions present in the chamber are detected by a change in the magnitude of said current.

2. The device according to claim 1, further comprising a display.

3. The device according to claim 1, further comprising an amperometry circuit that measures current through the CNM film.

4. The device according to claim 1, wherein a voltage applied across the pads in the range from about 0.01V to about 6.0V allows detection of ions as a modulation of current flowing through the CNM film.

5. The device according to claim 4, wherein the voltage is in the range from about 0.5V to about 3.0V.

6. The device according to claim 1 having a gain of about $10^4$ to $10^7$.

7. The device according to claim 1, wherein the CNM film consists of a plurality of SWCNT which are metallic, semi-conducting, or a mixture thereof.

8. The device according to claim 1, wherein the CNM film consists of graphene and the graphene is single atomic layer thickness.

9. The device according to claim 1, wherein the strip of CNM film has a width in the range from about 20 nm to about 100 μm.

10. The device according to claim 1, wherein the strip of CNM film has a length in the range from about 10 nm to about 1 mm.

11. The device according to claim 1 wherein the insulating substrate comprises a material selected from the group consisting of: Si, $SiO_2$, polydimethylsiloxane (PDMS), SU-8 photoresist, and poly(methyl methacrylate) (PMMA).

12. The device according to claim 1, wherein the thickness of the CNM film is in the range from about 11 nm to about 100 nm and its surface area is in the range from about 200 nm² to about 1.5 mm².

13. The device according to claim 1, wherein the weight of the device is in the range from about 100 µg to about 1 g.

14. A method of measuring the presence of ionizing radiation in an environment, the method comprising:
(a) providing a device comprising:
an insulating substrate;
first and second metallic contact pads disposed on a surface of the substrate;
a strip of carbon-based nanomaterial (CNM) film, the strip having a first end and a second end, the first end in contact with the first pad and the second end in contact with the second pad, wherein said strip of CNM film consists of graphene or a plurality of single-walled carbon nanotubes (SWCNT); and
a sealed housing enclosing the substrate, pads, and CNM film and forming a chamber; wherein the chamber comprises a gas that becomes ionized by radiation incident on the device; and wherein a potential difference applied across the pads causes current to flow through the CNM film and ions present in the chamber are detected by a change in the magnitude of said current;
(b) measuring current through the CNM film of the device; and
(c) comparing the current to a standard curve correlating current flow to known amounts of ionizing radiation for the device to quantify said ionizing radiation.

15. A method of quantifying an ionizing radiation, the method comprising:
(a) providing a device comprising:
an insulating substrate;
first and second metallic contact pads disposed on a surface of the substrate;
a strip of carbon-based nanomaterial (CNM) film, the strip having a first end and a second end, the first end in contact with the first pad and the second end in contact with the second pad, wherein said strip of CNM film consists of graphene or a plurality of single-walled carbon nanotubes (SWCNT); and
a sealed housing enclosing the substrate, pads, and CNM film and forming a chamber; wherein the chamber comprises a gas that becomes ionized by radiation incident on the device; and wherein a potential difference applied across the pads causes current to flow through the CNM film and ions present in the chamber are detected by a change in the magnitude of said current;
(b) exposing the device to the ionizing radiation;
(c) measuring a change in current flow through the CNM film of the device upon exposure to the ionizing radiation; and
(d) comparing the change in current flow to a standard curve correlating changes in current flow to known amounts of ionizing radiation to quantify said ionizing radiation.

16. The method according to claim 14, wherein the strip of CNM film consists of a plurality of SWCNT which are metallic, semi-conducting, or a mixture thereof.

17. The method according to claim 14, wherein the CNM film consists of graphene and the graphene is single atomic layer thickness.

18. The device according to claim 15, wherein the CNM film consists of a plurality of SWCNT which are metallic, semi-conducting, or a mixture thereof.

19. The device according to claim 15, wherein the CNM film consists of graphene and the graphene is single atomic layer thickness.

* * * * *

UNITED STATES PATENT AND TRADEMARK OFFICE
CERTIFICATE OF CORRECTION

PATENT NO.          : 10,036,728 B2
APPLICATION NO.     : 14/441218
DATED               : July 31, 2018
INVENTOR(S)         : Bo Li et al.

Page 1 of 1

It is certified that error appears in the above-identified patent and that said Letters Patent is hereby corrected as shown below:

In the Specification

Column 1, Line 12, insert the following:
--STATEMENT REGARDING FEDERALLY SPONSORED RESEARCH OR DEVELOPMENT
This invention was made with government support under Grant Number ECCS0925566 awarded by the National Science Foundation. The government has certain rights in the invention.--

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*